(12) United States Patent
Park et al.

(10) Patent No.: US 9,249,153 B2
(45) Date of Patent: Feb. 2, 2016

(54) PHARMACEUTICAL COMPOSITION FOR TREATING AGING-ASSOCIATED DISEASES, CONTAINING PROGERIN EXPRESSION INHIBITOR AS ACTIVE INGREDIENT, AND SCREENING METHOD OF SAID PROGERIN EXPRESSION INHIBITOR

(75) Inventors: Bum Joon Park, Busan (KR); Nam Chul Ha, Busan (KR); Gyu Yong Song, Daejeon (KR); Ji Hyun Lee, Daejeon (KR); Su Jin Lee, Busan (KR); Youn Sang Jung, Gyeongsangnam-do (KR)

(73) Assignees: PUSAN NATIONAL UNIVERSITY INDUSTRY-UNIVERSITY COOPERATION FOUNDATION, Busan (KR); THE INDUSTRY & ACADEMIC COOPERATION IN CHUNGNAM NATIONAL UNIVERSITY, Daejeon (KR)

( * ) Notice: Subject to any disclaimer, the term of this patent is extended or adjusted under 35 U.S.C. 154(b) by 157 days.

(21) Appl. No.: 14/005,558

(22) PCT Filed: Mar. 19, 2012

(86) PCT No.: PCT/KR2012/001953
§ 371 (c)(1),
(2), (4) Date: Oct. 16, 2013

(87) PCT Pub. No.: WO2012/128521
PCT Pub. Date: Sep. 27, 2012

(65) Prior Publication Data
US 2014/0039010 A1    Feb. 6, 2014

(30) Foreign Application Priority Data

Mar. 18, 2011 (KR) .................... 10-2011-0024308
Mar. 16, 2012 (KR) .................... 10-2012-0027028

(51) Int. Cl.
*A61K 31/352* (2006.01)
*C07D 493/04* (2006.01)
*A61K 31/70* (2006.01)
*A61K 31/7088* (2006.01)
*G01N 33/50* (2006.01)
*A61K 31/713* (2006.01)

(52) U.S. Cl.
CPC ............ *C07D 493/04* (2013.01); *A61K 31/352* (2013.01); *A61K 31/70* (2013.01); *A61K 31/7088* (2013.01); *A61K 31/713* (2013.01); *G01N 33/5008* (2013.01); *G01N 33/5011* (2013.01); *G01N 2500/00* (2013.01); *G01N 2800/7042* (2013.01)

(58) Field of Classification Search
None
See application file for complete search history.

(56) References Cited

U.S. PATENT DOCUMENTS 7,838,531 B2    11/2010    Gordon et al.
2008/0131375 A1    6/2008    Gordon et al.

FOREIGN PATENT DOCUMENTS

KR    2008-0004332 A    1/2008
WO    2008-004817 A1    1/2008

OTHER PUBLICATIONS

"Decursin: A Cytotoxic Agent and Protein Kinase C Activator from the Root of Angelica gigas" by Ahn et al., Planta Med. 62, 7-9 (1996).*
Capell, B. C. et al., "Inhibiting farnesylation of progerin prevents the characteristic nuclear blebbing of Hutchinson-Gilford progeria syndrome", Proc Natl Acad Sci U S A, Sep. 6, 2005, vol. 102, No. 36, pp. 12879-02884.
Lee, Kyeong et al., "Synthesis of (S)-( + )-decursin and its analogues as potent inhibitors of melanin formation in B16 murine melanoma cells", Eur. J. Med. Chem., Dec. 2010, vol. 45, No. 12, pp. 5567-5575.

* cited by examiner

*Primary Examiner* — Theodore R West
(74) *Attorney, Agent, or Firm* — Revolution IP, PLLC

(57) ABSTRACT

Disclosed are a method for treating an aging-related disease and a method for screening a therapeutic agent for an aging-related disease. The method for treating an aging-related disease includes administering to a subject a progerin expression inhibitor as an active ingredient. The method for screening a therapeutic agent for an aging-related disease includes selecting a candidate drug inhibitory of progerin expression.

3 Claims, 26 Drawing Sheets

Fig.8
A
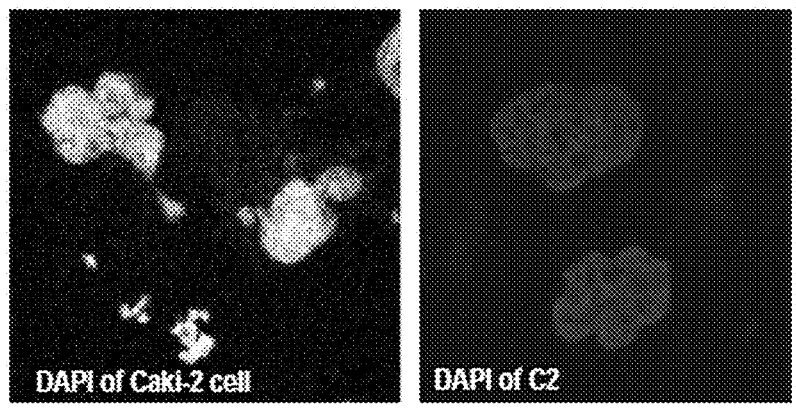
B
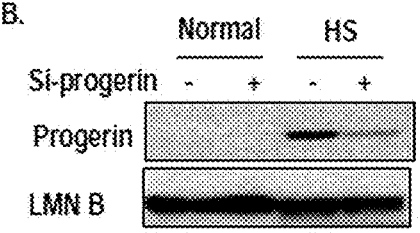
C
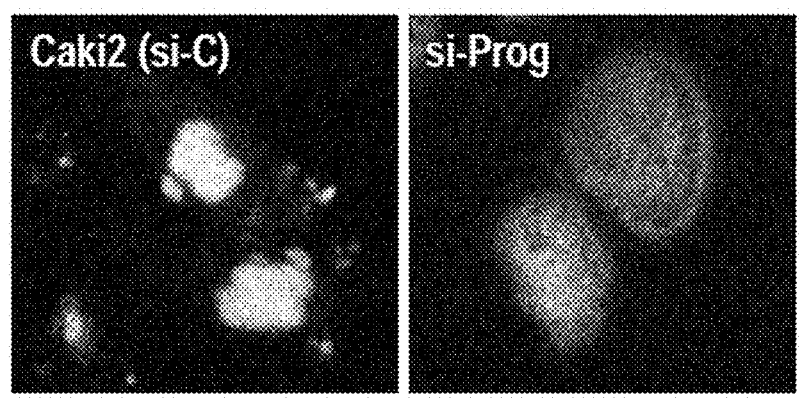

Fig. 9
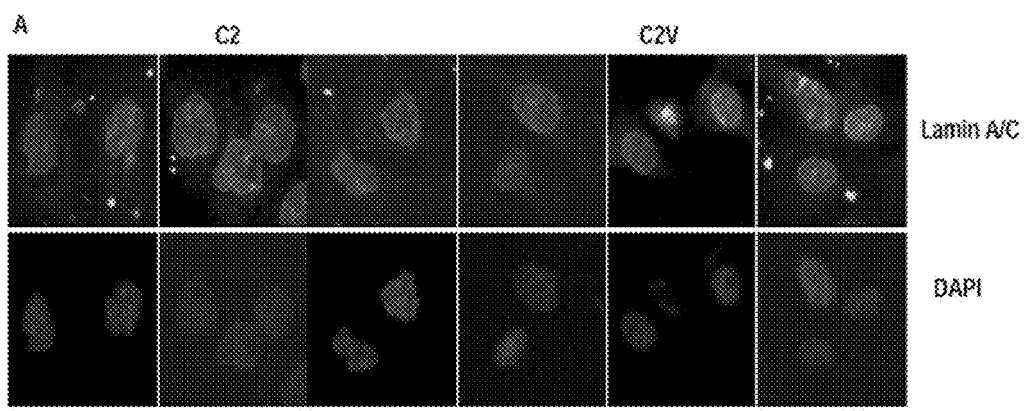
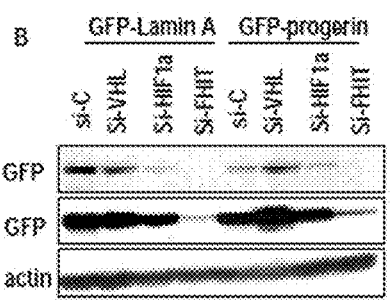
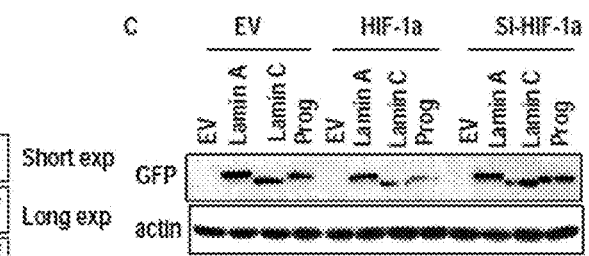
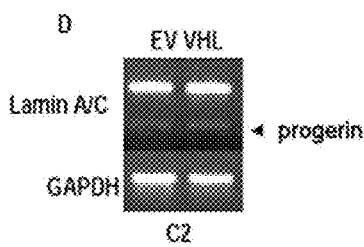

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Forward primer for lamin A/C

<400> SEQUENCE: 1
aaggagatga cctgctccat c                                       21

```
<210> SEQ ID NO 2
<211> LENGTH: 21
<212> TYPE: DNA
<213> ORGANISM: Artificial Sequence
<220> FEATURE:
<223> OTHER INFORMATION: Reverse primer for lamin A/C

<400> SEQUENCE: 2
tttctttggc ttcaagcccc c                                      21

<210> SEQ ID NO 3
<211> LENGTH: 21
<212> TYPE: DNA
<213> ORGANISM: Artificial Sequence
<220> FEATURE:
<223> OTHER INFORMATION: Forward primer for GAPDH

<400> SEQUENCE: 3
atcttccagg agcgagatcc c                                      21

<210> SEQ ID NO 4
<211> LENGTH: 21
<212> TYPE: DNA
<213> ORGANISM: Artificial Sequence
<220> FEATURE:
<223> OTHER INFORMATION: Reverse primer for GAPDH

<400> SEQUENCE: 4
agtgagcttc ccgttcagct c                                      21
```

PHARMACEUTICAL COMPOSITION FOR TREATING AGING-ASSOCIATED DISEASES, CONTAINING PROGERIN EXPRESSION INHIBITOR AS ACTIVE INGREDIENT, AND SCREENING METHOD OF SAID PROGERIN EXPRESSION INHIBITOR

CROSS REFERENCE TO PRIOR APPLICATIONS

This application is a National Stage Application of PCT International Patent Application No. PCT/KR2012/001953 filed on Mar. 19, 2012, under 35 U.S.C. §371, which claims priority to Korean Patent Application Nos. 10-2011-0024308 filed on Mar. 18, 2011 and 10-2012-0027028 filed on Mar. 16, 2012 which are all hereby incorporated by reference in their entirety.

SEQUENCE LISTING

An attached Sequence Listing (i. Name: SEQCRF_02280-1005, ii. Date of Creation: Sep. 17, 2013, and iii. Size: 2 KB) is concurrently filed with the 35 U.S.C. 371 National Stage Application of PCT International Application No. PCT/KR2012/001953. The entire contents of each of the above-identified Sequence Listings are hereby incorporated by reference.

TECHNICAL FIELD

The present invention relates to a pharmaceutical composition for the treatment of aging-related diseases, comprising a progerin expression inhibitor as an active ingredient, and a method for screening the same.

More particularly, the present invention relates to a novel compound disruptive of binding between progerin and lamin A, a pharmaceutical composition for treating aging-related diseases comprising the same, and a method for screening an inhibitor against binding between progerin and lamin A.

BACKGROUND ART

Renal cell carcinomas (RCC) are a frequent genitourinary malignancy with a morphological characteristic of an irregular nuclear shape, which is used as the index of RCC grading. In addition, p53 inactivation without genetic mutation and radiation-resistance are also suggested as the hallmark of RCC. In contrast, pVHL (Hippel-Lindau tumor suppressor protein) is frequently mutated from the early stage of RCC. However, molecular mechanisms have not yet been elucidated for a pleomorphic nucleus, p53 inactivation and radiation resistance.

Cancer is well defined as an aging related disease and also as a genetic disease. It has been clearly demonstrated why aged populations shows higher susceptibility to cancer. In general, it has been explained by multistep carcinogenesis. To reach malignant cancer, normal cells should accumulate significant genetic mutation. Thus, cancer formation requires a long period for development. However, in the case of the familial cancer syndromes including Li-fraumeni syndrome, von Hippel Lindau, and familial adenomatosis colis, the tumor formation thereof does not takes much time, and even rapidly progresses under a certain condition. In this regard, a recent, very interesting report has claimed that the biological function of the strong tumor suppressor p53 is declined in the aging process. Since p53 is a gatekeeper tumor suppressor, its functional decline may promote cancer development. Thus aging related change of the cellular context or gene expression profiling which can suppress the p53 function would be an important clue to understanding carcinogenesis in aged populations.

RCC is well known as an age related cancer. Its onset, although not high in young populations, is obviously increased in the aging process. In addition, RCC shows nuclear irregularity and resistance to IR treatment. However, the genetic mutation of p53, which has been suggested as the cause of IR-resistance, is very low. These features indicate that there might be a novel mechanism that can suppress the p53 function in RCC.

An additional significant genetic event of RCC is frequent mutation of pVHL. Although pVHL has been cloned from the human cancer syndrome von Hippel Lindau, its genetic mutation is known to reach 70% in primary clear cell renal carcinoma. As an E3 ligase, pVHL serves to degrade HIF-1a and block transcriptional activity. Since HIF-1a induces VEGF, EPO, and other pro-angiogentic factors in response to hypoxia, the activation of HIF-1a seems to be important for cancer progression, in particular, tumor-angiogenesis progression. However, in many kinds of solid cancers, HIF-1a can be stabilized and activated as a hypoxic condition is established at the inner cell mass of a tumor. In contrast, the deletion or functional loss of pVHL seems to be inessential for earlier carcinoma development. Moreover, angiogenesis is required at a late stage of cancer and the kidney is histologically characterized by plenty of well organized blood vessels. Hence, pVHL loss for achieving angiogenesis in the early stage of RCC is not critical for tumor formation. In fact, pVHL deletion is not detected in other kinds of invasive cancers. Thus, these features suggest that a novel tumor suppressing role of pVHL would exist and should be related with an RCC-specific function.

Taking into full consideration the fact that the onset of RCC dramatically increases in the aging process, the p53 function declines even without a genetic mutation, and pVHL is frequently mutated at an early stage, the present inventors proposed the hypothesis that the loss of pVHL would be related with aging-related gene expression, which can suppress the p53 function. To explore the hypothesis, a focus was made on the nuclear irregularity of RCC, which resembles the nuclear deformation in Hutchinson-Gilford progeroid syndrome (HGPS), discovering that progerin, a causal gene of HGPS, is expressed in aged cells.

In this context, the present inventors made an examination of relationship between the characteristics of RCC and the elevated expression of progerin, and found that the elimination of progerin can ameliorate the nuclear irregularity of RCC and restore p53 responsibility to DNA damage, and that both the elevated expression of progerin and the inactivation of p53 are attributable to pVHL dysfunction. In addition, pVHL can interact with progerin and block the progerin-induced p14/ARF inactivation whereas progerin sequesters p14, resulting in the inactivation of p53 and nuclear irregularity. It was also found that progerin expression can be detected in human leukemia samples and derived primary cell lines. From these data, progerin expression was discovered to be important for cancer progression, in particular, in an aged population, which leads to the present invention.

Expression of progerin can induce several morphological changes such as nuclear irregularity and a reduction of nuclear-plasmic Lamin A (LMN A). In fact, reduction or knock down of Prg can rescue the nuclear deformation, indicating that gained function of progerin is a causal factor for HGPS. In addition, it has been reported that progerin is accumulated in aged normal fibroblasts and evokes nuclear deformation. In iPSC (induced pluripotent stem cells) of HGPS patient, Prg as well as LMN A/C expression are obviously reduced and cellular senescence markers including nuclear deformation, H3K9me3, and SA-β-gal, are restored. In contrast, differentiated HGPS cells re-express the senescence markers, following progerin expression.

Since aging phenotypes and progression of HGPS seem to resemble normal aging or senescence processes, the present inventors investigated the function of progerin in cellular senescence through a study on HGPS, and found that a senescence progress proceeds with the interaction of progerin with Lamin A. Inhibitors against the interaction were excavated by chemical screening and evidenced to exert therapeutic effects on aging-related diseases, leading to the present invention.

DISCLOSURE

Technical Problem

It is an object of the present invention to provide a pharmaceutical composition for the treatment of an aging-related disease, comprising a progerin expression inhibitor as an active ingredient.

It is another object of the present invention to provide a method for screening a therapeutic drug for aging-related diseases, comprising selecting a candidate drug inhibitory of progerin expression.

It is a further object of the present invention to provide a novel compound inhibitory of binding between progerin and Lamin A.

It is a still further object of the present invention to provide a pharmaceutical composition for the prevention and treatment of aging-related disease, comprising the novel compound as an active ingredient.

It is still another object of the present invention to provide a method for screening a therapeutic drug for aging-related diseases, comprising selecting a candidate drug inhibitory of binding between progerin and Lamin A.

Technical Solution

In accordance with an aspect thereof, the present invention addresses a pharmaceutical composition for the treatment of an aging-related disease, comprising a progerin expression inhibitor as an active ingredient.

In one embodiment, the progerin expression inhibitor may be a pVHL (Hippel-Lindau tumor suppressor protein)-progerin binding promoter, or an RNA molecular inhibitory of progerin expression, selected from the group consisting of an antisense-RNA, interference RNA, short-hairpin RNA, and small interfering RNA (siRNA).

Preferably, the progerin expression inhibitor may promote binding between pVHL (Hippel-Lindau tumor suppressor protein) and progerin to suppress the binding of progerin to p14, thereby preventing p53 from being inactivated.

In one embodiment, the aging-related disease may be a cancer selected from the group consisting of renal cancer, leukemia and prostate cancer, or progeria selected from among Werner syndrome and Hutchinson-Gilford progeroid syndrome.

Aging-related diseases, such as RCC, are known to allow an elevated expression of progerin. It is found in the present invention that when the expression level of progerin is reduced, nuclear irregularity, characteristic of RCC, is improved while the responsibility of p53 to DNA damage is restored by the elimination of progerin. pVHL interacts with progerin to block progerin-induced p14/AFR inactivation, which leads to p14-mediated p53 activation, thus suppressing tumorigenesis. In addition, progerin expression was detected in human leukemia samples and primary cell lines derived from the samples. Hence, the expression of progerin was observed to play a significant role in cancer progression of cancer, in particular, in an aged population.

Accordingly, a material which can inhibit the expression of progerin particularly by stimulating binding between pVHL and progerin may be a promising candidate drug for the therapy of aging-related diseases, such as RCC, leukemia, prostate cancer, progeria, etc.

The pharmaceutical composition of the present invention may further comprise an appropriate carrier, excipient or diluent if it is used typically in the art.

Examples of the carrier, excipient or diluent useful in the invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methylhydrobenzoate, propylhydroxybenzoate, talc, and magnesium stearate, but are not limited thereto.

The pharmaceutical composition may be formulated into an oral dosage form, such as a powder, a granule, a tablet, a capsule, a suspension, an emulsion, a syrup, and an aerosol, or may be in the form of a topical agent, a suppository, or a sterile injection.

For formulation, a diluent or excipient such as a filter, a thickener, a binder, a humectants, a disintegrant, a surfactant, etc. may be combined with the active ingredient of the present invention. Solid preparations intended for oral administration of the compound of the present invention may take the form of tablets, pills, powders, granules, capsules, and the like. In regards to these solid agents, the compound of the present invention may be formulated in combination with at least one excipient such as starch, calcium carbonate, sucrose, lactose, or gelatin.

Further, a lubricant such as magnesium stearate, talc, or the like may also be added. Liquid preparations intended for oral administration include suspensions, internal use solutions, emulsions, syrups, and the like. In addition to simple diluents such as water or liquid paraffin, various excipients, such as wetting agents, sweetening agents, aromatics, preservatives, and the like may be contained in the liquid preparations.

Also, the compound of the present invention may be administered via a non-oral route. For this, sterile aqueous solutions, non-aqueous solvents, suspensions, emulsions, lyophilizates, suppositories, and the like may be used. Injectable propylene glycol, polyethylene glycol, vegetable oils such as olive oil, and esters, such as ethyl oleate may be suitable for non-aqueous solvents and suspensions. The basic materials of suppositories include Witepsol, macrogol, Tween 61, cacao butter, laurin butter, glycerol, and glycerogelatin.

The effective dosage of the active ingredient in accordance with the present invention depends on various factors, including the patient's age, gender, and weight, the severity and kind of disease, etc. The active ingredient according to the present invention may be administered in a single dosage or may be divided into multiple dosages per day. Thus, the dosage limits the scope of the present invention in no way.

The pharmaceutical composition may be administered into mammals such as rats, mice, livestock, humans, etc. via various routes. All types of administration may be expected. For example, oral, rectal, or intravenous, intramuscular, subcutaneous, intracervical or intracerebroventricular routes may be taken.

In accordance with another aspect thereof, the present invention addresses a method for screening a therapeutic drug for an aging-related disease, comprising selecting a candidate drug inhibitory of progerin expression.

In a preferable embodiment, the method comprises culturing cells with pVHL (Hippel-Lindau tumor suppressor protein) and progerin in the presence of a candidate drug; and quantifying progerin expression in the cells to select the drug candidate which stimulates pVHL (Hippel-Lindau tumor suppressor protein)-progerin binding to inhibit interaction between progerin and p14.

In this regard, the aging-related disease may be a cancer selected from among renal cancer, leukemia and prostate cancer; or a Werner syndrome or a Hutchinson-Gilford progeroid syndrome.

In accordance with a further aspect thereof, the present invention addresses a compound, represented by the following Chemical Formula 1 or 2, or a pharmaceutically acceptable salt:

[Chemical Formula 1]

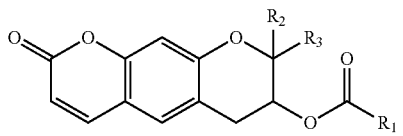

[Chemical Formula 2]

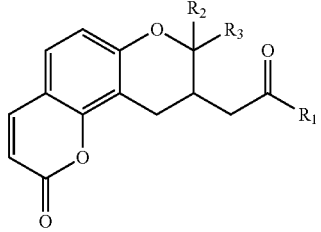

wherein, $R_1$ is

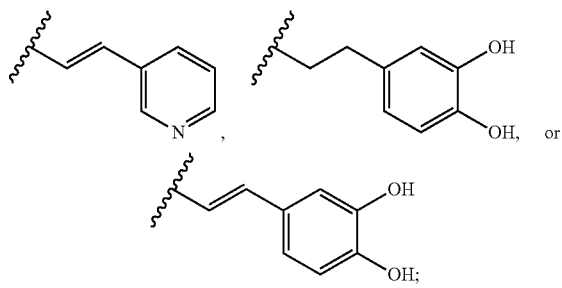

$R_2$ and $R_3$ are independently hydrogen or $C_{1-4}$ alkyl.

According to one embodiment, $R_1$ is

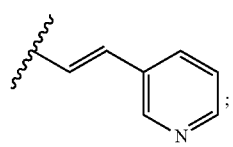 [SMILES: */C=C/c1cccnc1]

and $R_2$ and $R_3$ are each methyl in Chemical Formula 1.

The compound of Chemical Formula 1 or 2 according to the present invention may be in the form of a pharmaceutically acceptable salt. Useful is an acid addition salt formed with a pharmaceutically acceptable free acid which may be an organic acid or an inorganic acid. Examples of the inorganic acid include chloric acid, bromic acid, sulfuric acid, sulfurous acid, and phosphoric acid. Among the organic acid useful in the present invention are citric acid, maleic acid, fumaric acid, gluconic acid, methane sulfonic acid, acetic acid, glycolic acid, succinic acid, tartaric acid, 4-toluenesulfonic acid, galacturonic acid, embonic acid, glutamic acid, and aspartic acid. Preferred are hydrochloric acid as an inorganic acid, and methane sulfonic acid as an organic acid.

Not only the compound of Chemical Formula 1 or 2 and pharmaceutically acceptable salts thereof, but also solvates and hydrates prepared therefrom are within the scope of the present invention.

As elucidated in the following example section, the compound of Chemical Formula 1 or 2 of the present invention is highly suppressive of binding between progerin and Lamin A, so that it can be effectively applied to the prevention and treatment of progerin-induced aging-related diseases. Leading to the present invention, the intensive and thorough research into progerin-induced senescence mechanism of the present inventors resulted in the finding that interaction between progerin and Lamin A is responsible for cellular senescence, and allowed the excavation of inhibitors against the interaction.

Thus, contemplated in accordance with a still further aspect of the present invention is a pharmaceutical composition for the prevention or treatment of an aging-related disease, comprising a compound represented by the following Chemical Formula 1 or 2, or a pharmaceutically acceptable salt thereof.

[Chemical Formula 1]

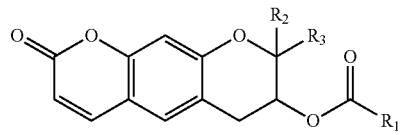

[Chemical Formula 2]

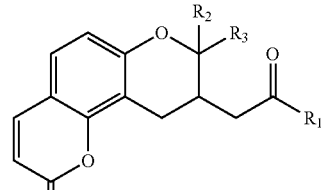

wherein, $R_1$ is

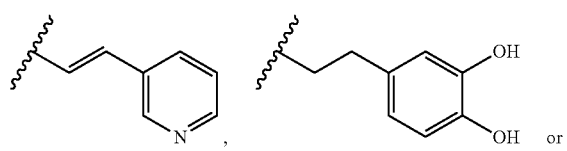

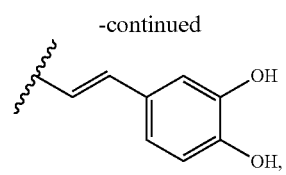

and
R$_2$ and R$_3$ are independently hydrogen or C$_{1-4}$ alkyl.
In Chemical Formula 1, preferably, R$_1$ is

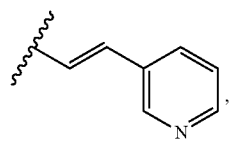 [SMILES: */C=C/c1cccnc1]

and R$_2$ and R$_3$ are each methyl.

In one embodiment of the present invention, the compound of Chemical Formula 1 or 2 has the activity of suppressing progerin from binding Lamin A, and can be applied to the therapy or prophylaxis of aging-related diseases.

As further explained in the following example section, the compound of Chemical Formula 1 or 2 of the present invention is highly suppressive of binding between progerin and Lamin A, so that it can be effectively applied to the prevention and treatment of aging-related diseases caused by the interaction of progerin with Lamin A.

Accordingly, the present invention pertains to a pharmaceutical composition for the prevention or treatment of an aging-related disease, comprising a compound represented by Chemical Formula 1 or or a pharmaceutically acceptable salt thereof as an active ingredient, the use of a compound represented by Chemical Formula 1 or 2 or a pharmaceutically acceptable salt thereof in the preparation of an therapeutic agent for aging-related diseases, and a method for treating an aging-related disease, comprising administering a compound represented by Chemical Formula 1 or 2 or a pharmaceutically acceptable salt thereof in a therapeutically effective amount to a subject in need thereof.

In one embodiment, the again-related disease is a cancer or progeria. In this regard, the cancer may be selected from among renal cancer, leukemia, and prostate cancer while the progeria may be the Werner syndrome or the Hutchison-Gilford progeroid syndrome.

In another embodiment, the pharmaceutical composition for the prevention or treatment of aging-related diseases according to the present invention may comprise the compound of Chemical Formula 1 or 2 or a pharmaceutically acceptable salt thereof in an amount of 0.01 to 90 weight parts, preferably in an amount of 0.1 to 90 weight parts, more preferably in an amount of 1 to 90 weight parts, and most preferably in an amount of 10 to 90 weight parts, based on 100 weight parts of the composition. The amount is not limited thereto, and may vary depending on the state of the patient, and the kind and progression of the disease to be treated.

According to a further embodiment, the pharmaceutical composition for the prevention or treatment of aging-related diseases in which the compound of Chemical Formula 1 or 2 or a pharmaceutically acceptable salt thereof is employed as an active ingredient may further comprise at least one additive selected from the group consisting of a carrier, an excipient, a disintegrant, a sweetener, a coating agent, an effervescent, a lubricant, a glidant, an aromatic, an antioxidant, a buffer, a bacteriostat, a diluent, a dispersant, a surfactant, and a binder.

Concrete examples of the carrier, excipient or diluent useful in the invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methylhydrobenzoate, propylhydroxybenzoate, talc, and magnesium stearate, and mineral oil. Solid preparations intended for oral administration of the compound of the present invention may take the form of tablets, pills, powders, granules, capsules, and the like. In regards to these solid agents, the compound of the present invention is formulated in combination with at least one excipient such as starch, calcium carbonate, sucrose, lactose, or gelatin. In addition, a lubricant such as magnesium stearate, talc, or the like may also be added. Liquid preparations intended for oral administration include suspensions, internal use solutions, emulsions, syrups, and the like. In addition to simple diluents such as water or liquid paraffin, various excipients, such as wetting agents, sweetening agents, aromatics, preservatives, and the like may be contained in the liquid preparations. Also, the compound of the present invention may be administered via a non-oral route. For this, sterile aqueous solutions, non-aqueous solvents, suspensions, emulsions, lyophilizates, suppositories, and the like may be used. Injectable propylene glycol, polyethylene glycol, vegetable oils such as olive oil, and esters such as ethyl oleate may be suitable for non-aqueous solvents and suspensions. The basic materials of suppositories include Witepsol, macrogol, Tween 61, cacao butter, laurin butter, glycerol, and glycerogelatin.

In another embodiment of the present invention, the pharmaceutical composition for the prevention or treatment of aging-related diseases comprising the compound of Chemical Formula 1 or 2 or a pharmaceutically acceptable salt thereof as an active ingredient may be in the form of a granule, a powder, a coated tablet, a tablet, a pill, a suppository, a gel, a syrup, a juice, a suspension, an emulsion, an eye drop, or a liquid.

The pharmaceutical composition according to one embodiment of the present invention may be administered to a subject via intravenous, intra-arterial, intraperitoneal, intramuscular, intrathoracic, transdermal, intranasal, topical, rectal, oral, intraocular or intradermal routes or by inhalation.

The effective dosage of the compound of Chemical Formula 1 or 2 in accordance with the present invention depends on various factors, including the patient's condition and weight, the kind and severity of disease, the dosage form of drug, the route and time of administration, etc., and may be properly determined by those skilled in the art. The compound according to the present invention may be administered in a single dosage or may be divided into multiple dosages per day at a daily dosage ranging from 0.01 to 1,000 mg/kg, preferably from 0.1 to 1,000 mg/kg, and more preferably from 0.1 to 100 mg/kg, but is not limited thereto.

As used herein, the term "subject" encompasses mammals including, but not limited to, humans.

In accordance with still another aspect thereof, the present invention addresses a method for screening a therapeutic agent for an aging-related disease, comprising selecting a candidate drug inhibitory of binding between progerin and Lamin A.

In one embodiment, the screening is carried out by: incubating progerin and fluoroprotein-labeled Lamin A in the presence of a candidate drug; and quantifying binding between progerin and the fluoroprotein-labeled Lamin A to select the candidate drug inhibitory of binding between progerin and Lamin A.

In another embodiment, the aging-related disease is a cancer or progeria wherein the cancer is selected from the group consisting of renal cancer, leukemia, and prostate cancer, and the progeria is selected from among a Werner syndrome and a Hutchinson-Gilford progeroid syndrome.

Advantageous Effects

Capable of suppressing the overexpression of progerin and inhibiting binding between progerin and Lamin A, the pharmaceutical composition of the present invention is effective at treating or preventing diseases caused by progerin expression and progerin-Lamin A binding, particularly, renal cancer, leukemia, prostate cancer, and progeria, which are more apt to occur in an aged population. In addition, the screening method of the present invention allows the specific selection of a drug which is simulative of binding between pVHL and progerin, or inhibitory of binding between progerin and Lamin A, thereby developing an effective therapeutic agent for a disease caused in an aged population, such as renal cancer, leukemia, prostate cancer, and progeria.

BRIEF DESCRIPTION OF THE DRAWINGS

FIG. 8 analyzes the nuclear morphology of RCC in terms of DAPI staining of Caki-2 (left) and C2 cells (A), the effect of si-progerin on progerin expression (B), and the effect of si-progerin on nuclear morphology (C).

FIG. 9 demonstrates progerin expression in an HIF-1a independent manner by pVHL in terms of the nuclear morphology of C2 cells and pVHL-stable transfected C2V cells (A), the effect of si-progerin on progerin expression (B), the effect of HIF-1a overexpression on progerin induction (C), and the effect of pVHL on progerin transcription (D).

MODE FOR INVENTION

Figure 1:
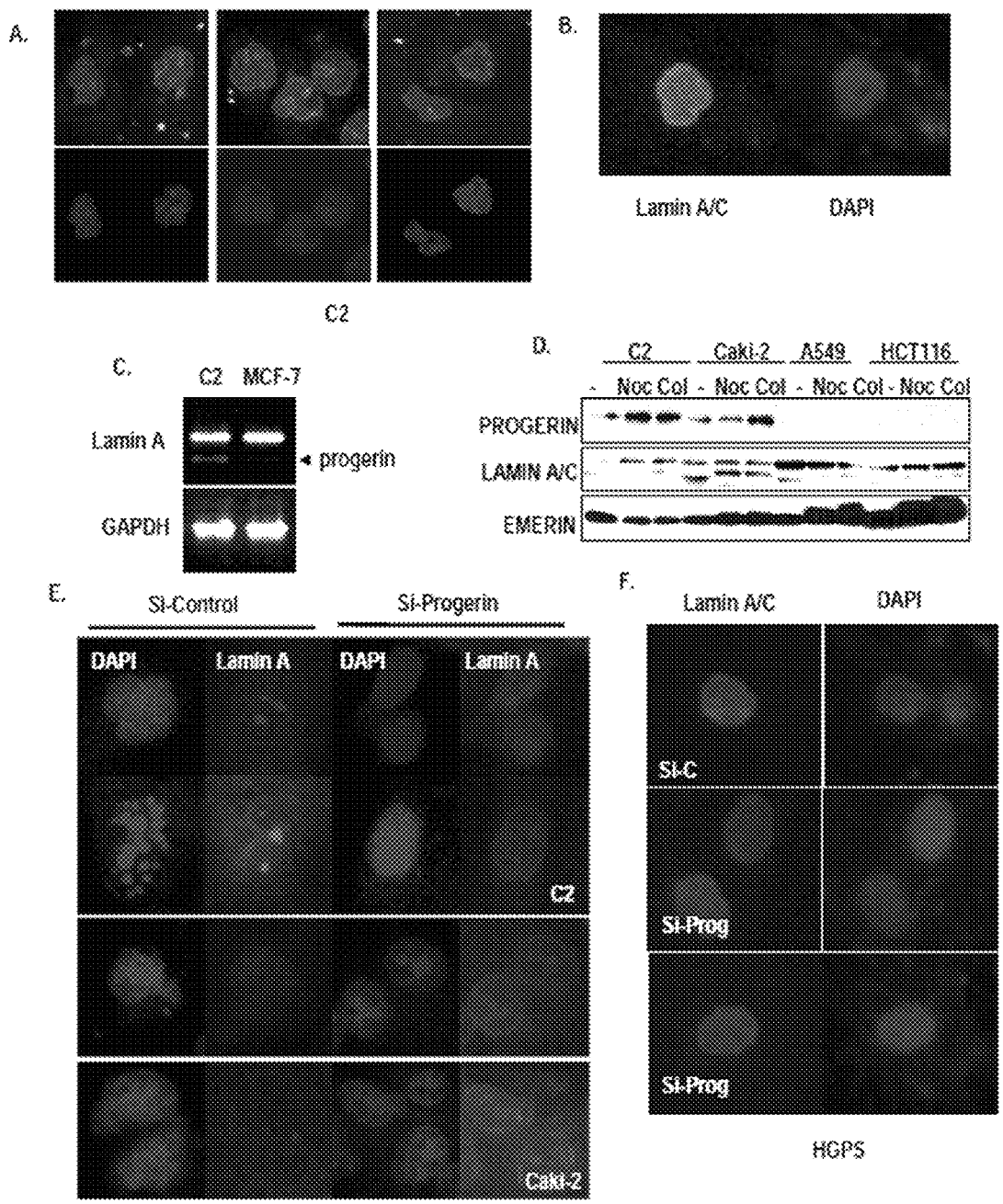
FIG. 1 demonstrates the responsibility of progerin for the nuclear irregularity of RCC in terms of the irregularity of nuclear membrane in the human RCC cell line C2 under a normal condition (A), the morphology of nuclear deformation of HGPS in RCC (B), the transcriptional expression of progerin in RCC (C), progerin expression at a translation level (D), the effect of si-progerin on the nuclear irregularity of RCC (E), and the effect of Si-progerin on nuclear morphology in HGPS (F).

A better understanding of the present invention may be obtained through the following example(s) which are set forth to illustrate, but are not to be construed as limiting the present invention.

Example 1

Senescence-Inhibiting Mechanism by Interaction Between Progerin and pVHL

1. Cell Cultures and Reagents

Some of the cell lines used in the present invention were obtained from ATCC, and maintained in RPMI-1640 (A549, HCT116) or DMEM (293) supplemented with 10% FBS and 1% antibiotic at 37° C. in a growth chamber. The other cell lines were granted from Dr. Jung Y J (Pusan National University), and maintained in the medium C2 (UMRC2), C2V (UMRC2V) or DMEM (CAKI2) supplemented with 10% FBS and 1% antibiotic at 37° C. in a growth chamber.

Human fibroblast cells from a Werner syndrome patient (AG03141; 30-year-old female), an HGPS patient (AG01972; 14-years-old female), and a normal person (GM 00038; 9-years-old female) were obtained from the Coriell Cell Repositories, and were maintained in EMEM, containing 15% FBS and 2 mM Glu without antibiotics.

Also, a purchase was made of general chemical inhibitors including nocodazol and colcemide from Calbiochem, p14/ARF (MS-850-P0) Emerin from Novocastra, various antibodies against progerin (sc-81611), Lamin A (sc-20680), GST (sc-138), GFP (sc-9996), VHL (sc-17780), p53 (DO-1) (sc-126), actin (sc-1616), MDM2 (sc-965) and His (sc-8036) from Santa Cruz, an anti-α-FLAG antibody (F3165) from sigma, and antibodies against p21 (#2946) and p-chk2 (#2661) from Cell signaling.

2. Vectors and Transfection

GFP-fused progerin and GFP-fused Lamin A expression vectors were kindly provided by Scaffidi and Misteli (NCI). pVHL mammalian expression vectors were obtained from Dr. Jung Y J (Pusan National University). A Myc-ARF vector and a p21-luciferase vector were purchased from Addgene. Si-progerin and si-p14 were designed as previously reported (Scaffidi and Misteli, 2005; Voorhoeve and Agami, 2005). For mammalian expression of these vectors, transfection was performed with the aid of Jetpei (Polyplus). In 150 nM NaCl solution, 1.5 µg of the vector was mixed with 1.5 µl of the Jetpei reagent. After incubation for 15 min at room temperature, the mixture was added to the cell. After 3 hrs, the 10% FBS medium was replaced by a serum-free medium.

3. Recombinant Proteins and GST-Pull Down

For use in protein-protein interaction analysis, Lamin A-C-terminal region (L-C), and progerin-C-terminal region (Prog) were amplified from 100 amino acids upstream of respective termination codons by PCR. Full-length p14 and VHL were also obtained by PCR and cloned into respective pGEX vectors. Each clone was confirmed by base sequencing. Using a nickel column, these recombinant proteins were purified.

For binding assay, GST-bead-fused Lamin A-C or progerin-C was incubated for 2 hrs at room temperature with a lysate of p14/ARF transfected-293 cells. On the other hand, GST-p14 or pVHL was incubated for 2 hrs at room temperature with a lysate of GFP-Lamin A or progerin-transfected 293 cells. After washing twice with PBS and once with RIPA, the precipitated materials were collected, and subjected into SDS-PAGE and Western blot analysis with anti-p14 and GST antibodies.

4. Immunoprecipitation and Western Blot (WB) Analysis

Whole cell lysates were prepared in RIPA buffer, and centrifuged at 14,000 rpm for 30 min. Twenty micrograms of cell extracts were separated by SDS-polyacrylamide gel electrophoresis and transferred onto a PVDF membrane. The membrane was incubated for 1 hr to overnight at 4° C. with an appropriated primary antibody, followed by reaction with a secondary antibody at room temperature for 1 hr. Peroxidase activity was detected by chemiluminescence with an ECL kit (Intron) as recommended by the manufacturer.

To examine interaction between pVHL and Lamin A, the protein extracts were added with an antibody against pVHL or Lamin A/C (2 g/sample). After incubation for 2 hrs at 4° C. with agitation, protein A and protein G were added. After washing twice with PBS, the precipitates were dissolved in RIPA buffer and SDS sample buffer.

5. Immunofluorescence (IF) Staining

Nuclear morphology was obtained through immunostaining. In this regard, cells transfected with predetermined vectors were fixed with 100% methanol for 10 min at 4° C. After washing with PBS, the cells were incubated in a blocking buffer (PBS+1% BSA+normal Goat Ab) for 1 hr. Then, the cells were washed twice with PBS, and incubated with an anti-Lamin A/C antibody in a blocking buffer (1; 200) for 2 hr and sequentially with an anti-Rabbit Ab-FITC or anti-Rabbit ab-Rhodamin in a blocking buffer (1:1000) for 2 hr. The cells were mounted on a slide, and stained for nuclei with DAPI. Immunofluorescence signals were detected by fluorescence microscopy (Zeiss).

6. RNA Isolation and RT-PCR

For RT-PCR, total cellular RNA was extracted using a Qiagen RNA extraction kit. After measurement of RNA concentration, 1 µg of total RNA was reverse transcribed to cDNA using random hexamers in the presence of MMLV RT (Invitrogen). RT-PCR was performed with the following specific primers:

```
Lamin A/C Forward:
5'- AAGGAGATGACCTGCTCCATC -3'      (SEQ ID NO: 1)

Reverse:
5'- TTTCTTTGGCTTCAAGCCCCC-3'       (SEQ ID NO: 2)

GAPDH Forward:
5'-ATCTTCCAGGAGCGAGATCCC-3'        (SEQ ID NO: 3)

Reverse:
5'-AGTGAGCTTCCCGTTCAGCTC-3'.       (SEQ ID NO: 4)
```

7. MTT Assay

To measure cell viability, cells were transfected with predetermined vectors or si-RNA for 24 hrs. After washing, the cells were treated with adriamycin and camptothecin for 2 hrs. For MTT assay, the cells were incubated with a 0.5 mg/ml MTT solution for 4 hr at 37° C. Excess solutions were removed, and the precipitates were dissolved in 200 µl of DMSO and quantified by reading absorbance at 540 nm.

8. Luciferase Assay

To measure p21 activity, a p21-luc vector was co-transfected, together with si RNAs, to 293 cells for 24 hrs. The cells were washed and treated with adriamycin for 2 hrs. After they were washed with a wash buffer (Promega), the cells were lyzed in a lysis buffer. Luciferase activity was determined using a luminometer.

9. Human Leukemia Samples

Blood samples of leukemia patients and normal persons were provided by the Pusan National University Hospital. WBC were collected from the blood samples and stored at −70° C. until use. Diagnosis followed the general procedure. To establish cell lines, the WBC were cultured in DMEM (supplemented with 15% FBS) and obtained as 3 different, stable cells.

10. Results

1) The Nuclear Irregularity of RCC Resulted from an Elevated Expression of Progerin.

The human RCC cell line UMRC2 (C2) showed similar nuclear irregularity similar to the nuclear deformation of HGPS cells (FIGS. 1A and 1B). Also, the same nuclear irregularity was observed in a Caki-2 cell line (FIG. 8A).

Since nuclear deformation in HGPS cells is responsible for the progerin expression, the progerin transcript in the RCC cell line C2 was examined by RT-PCR. Comparing to the breast cancer cell line MCF-7, C2 showed an elevated expression level of progerin (FIG. 1C). The progerin expression was measured by Western blot analysis (FIG. 1D).

Next, an examination was made to see whether progerin is responsible for the nuclear irregularity of RCC. For this, si-RNA against progerin was synthesized, and transfected into C2 and Caki2 cells. When progerin was eliminated, the RCC cell lines improved in nuclear irregularity (FIGS. 1E and 8C). In addition, the elimination of progerin increased Lamin A/C expression (FIGS. 1D and 1E).

Consistent with observation of the suppression effect of progerin on lamin A/C expression, the elimination of progerin ameliorated nuclear deformation in HGPS cells (FIG. 1F).

These data suggest that both the nuclear deformation of HGPS and the nuclear irregularity of RCC result from an elevated expression of progerin.

2) pVHL Regulates Progerin Expression

Since pVHL is frequently mutated in RCC, relationship between pVHL and nuclear deformation was examined. First, the nuclear morphology of C2 was compared with that of the pVHL-stable transfected cell line UMRC2V (C2V). C2 (C2V) was improved in nuclear morphology as pVHL was re-expressed therein (FIG. 9A).

To address how pVHL regulates progerin expression, the effect of pVHL on progerin expression was examined. Overexpression of pVHL suppressed progerin expression (FIG. 2A) whereas si-pVHL increased it (FIG. 2B). However, Lamin A expression was not affected by pVHL (FIGS. 2A and B).

Based on the fact that pVHL suppresses HIF-1a expression, the effect of HIF-1a on progerin expression was also examined. However, HIF-1a overexpression or knock down did not alter the progerin expression obviously (FIGS. 9B and 9C). These results indicate that pVHL-induced progerin suppression would be achieved through an HIF-1a-independent pathway.

To confirm the effect of pVHL on progerin, the expression of progerin in C2V was analyzed and compared to C2, by WB analysis. The expression of progerin was diminished in pVHL-expressed C2V cells (FIG. 2C). However, transcripts of progerin were not significantly suppressed by pVHL transfection (FIG. 2D), indicating that pVHL regulates progerin at a post-transcriptional level.

Also, pVHL acts as an E3 ligase. In this context, progerin was examined for pVHL-dependent half-life by the pulse-chase analysis. pVHL obviously suppressed the expression of progerin, but did not affect the expression of Lamin A (FIG. 2D). The pulse-chase analysis was performed by examining the cells for protein reduction rate for a predetermined period of time in the presence of cyclohexamide (CHX), a protein synthesis inhibitor.

To confirm the role of pVHL in progerin expression, cells were transfected with mutant pVHL and measured for progerin expression. Unlike wild-type pVHL, mutant pVHL with impaired E3-ligase ability did not suppress progerin expression (FIG. 2E).

Next, the effect of pVHL on the nuclear deformation of HGPS cells was investigated by IF staining with Lamin A/C, and WB analysis. Similar to RCC cells, pVHL overexpression ameliorated the nuclear morphology (FIG. 2F).

These results suggest that pVHL can suppress progerin expression by promoting protein turn-over.

3) Progerin Suppresses p53 Through Direct Interaction with pVHL

Figure 3:
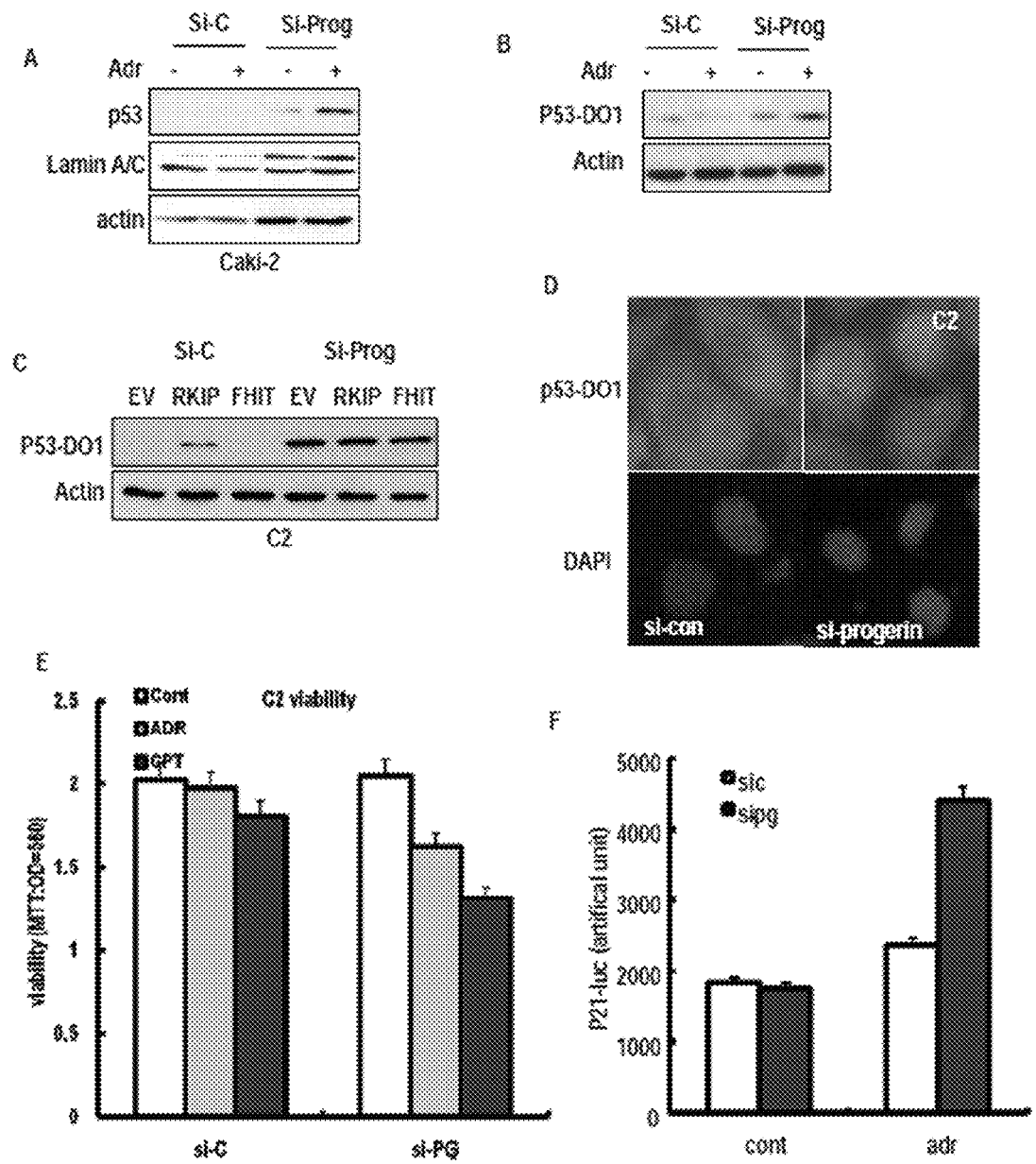
FIG. 3 demonstrate the inhibitory activity of progerin against p53 in terms of the effect of si-progerin on p53 expression in caki-2 cells (A), the effect of si-progerin on p53 expression in C2 cells (B), the effect of FHIT or RKIP on p53 expression in C2 cells (C), an immunostaining assay for p53 in si-progerin transfected C2 cells (D), the influence of si-progerin on the sensitivity of C2 cells to DNA damage (E), and the effect of Si-progerin on the transcriptional activity of p53 (F).
Figure 10:
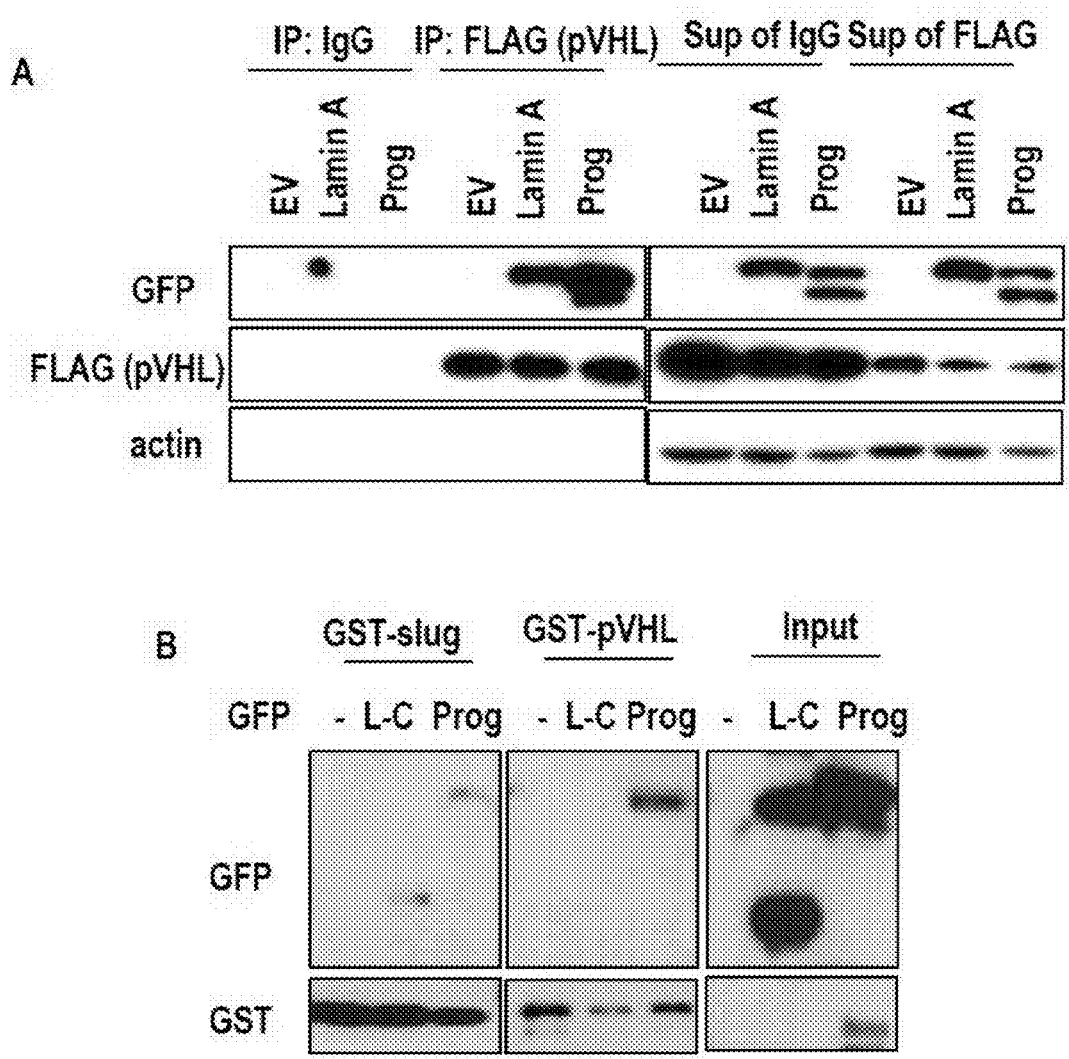
FIG. 10 shows direct relationship between pVHL and progerin in terms of the interaction of progerin and pVHL (A), and a GST-pull down assay (B).

Interaction between pVHL and progerin was determined by IP analysis. Both the proteins were co-precipitated by a pVHL (Flag) antibody (FIG. 10A). Although Lamin A was co-migrated with pVHL, binding affinity between pVHL-proegrin seemed to be stronger than that between pVHL and Lamin A. A GST-pull down assay showed direct binding between progerin-pVHL (FIG. 3B).

Since RCC is characterized by inactivating p53 without genetic mutation, the effect of well-known p53 inhibitors including MDM2, COP1 and Parc-ion p53 expression in C2 cell was examined. The knock down of these p53 inhibitors, however, did not induce the expression of p53 (FIG. 10A).

Figure 4:
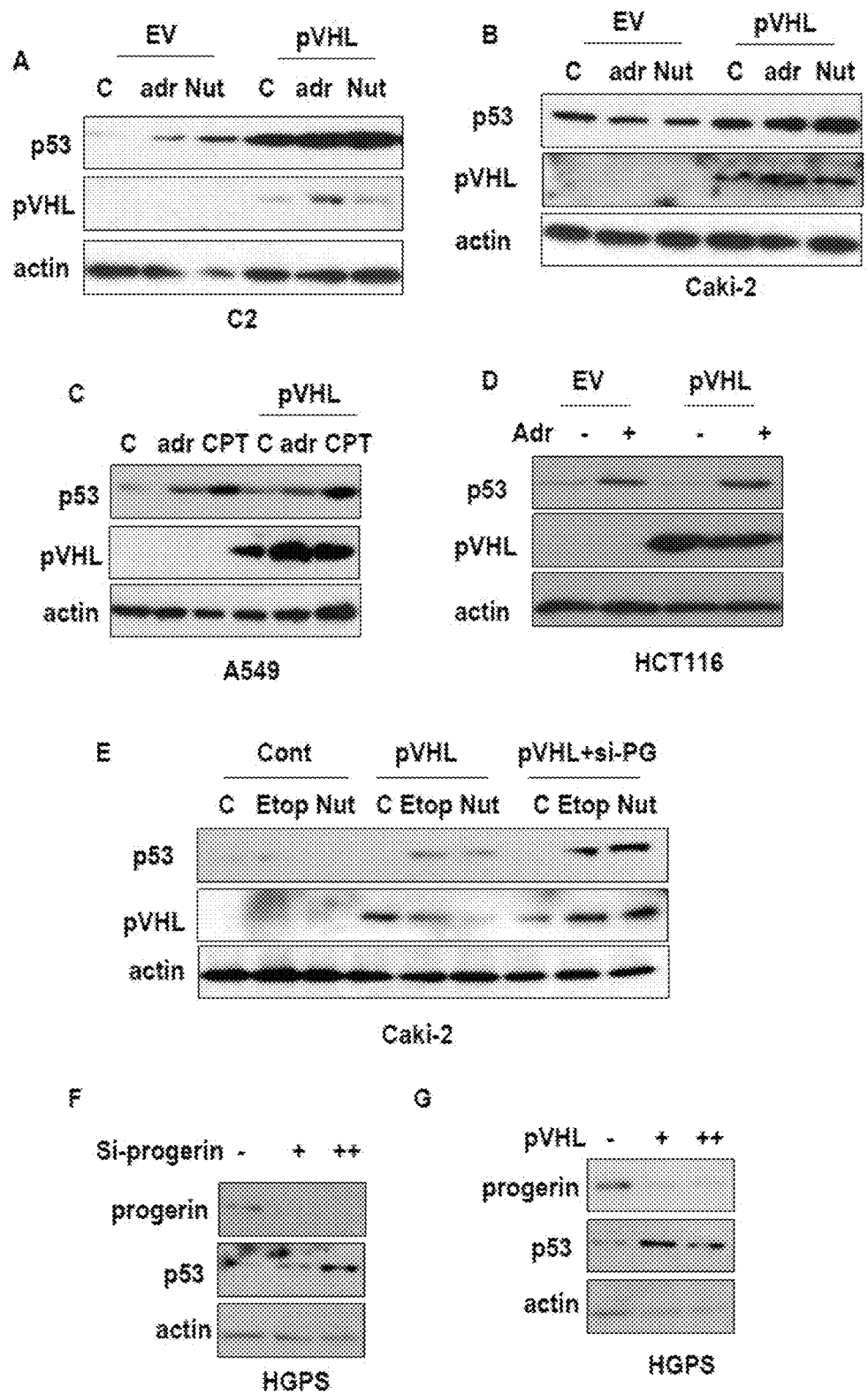
FIG. 4 demonstrates the involvement of progerin in pVHL-induced p53 activation in terms of the effect of pVHL transfection on p53 induction in C2 cells (A), the effect of pVHL on p53 induction in Caki-2 cells (B), the effect of pVHL on p53 induction in A549 (C), the effect of pVHL on p53 induction in HCT116 (D), the effect of pVHL on p53 induction Caki-2 cells in the presence of si-progerin (E), the effect of si-progerin on p53 induction in HGPS cells (F), and the effect of pVHL on p53 induction in HGPS cells (G).

The next focus was turned toward relationship between p53 inactivation and progerin expression. First, p53 expression in HGPS cells was examined. Compared to normal fibroblasts, HGPS cells were extremely low in p53 expression level (FIG. 10B), but the elimination of progerin could induce p53 expression (FIG. 10B). In addition, p53 expression and responsibility for DNA damage in Caki-2 were determined after transfection with si-progerin. Extremely low p53 expression and insensitivity to Adr were recovered by si-progerin (FIG. 4A). Similar results were also obtained from C2 cells (FIG. 4B).

FHIT and RKIP were known to be deleted in RCC. Data from an experiment on their involvement in the regulation of p53 in the RCC cell line showed that p53 expression, although partially induced by RKIP, was fully positively dependent on si-progerin (FIG. 4C). Similarly, si-progerin was also found to induce p53 expression, as evidenced by immune-fluorescence staining (FIG. 4D).

To confirm the re-activation of p53 in response to progerin knock down, the transcriptional activity of p53 was monitored using a p21-luc system. Treatment with Adr did not increase p21-luc expression in control C2 cells (FIG. 3D). In contrast, si-progerin could restore Adr-induced p21-luc activation (FIG. 3E).

An MTT assay was performed to monitor cell viability, giving the information that DNA damage-induced cell death was re-stored by si-progerin (FIG. 3F).

These results strongly suggest that an elevated expression of progerin can block p53-induced cell death and tumor suppression.

4) pVHL Activates p53 in a Progerin-Dependent Manner.

Figure 2:
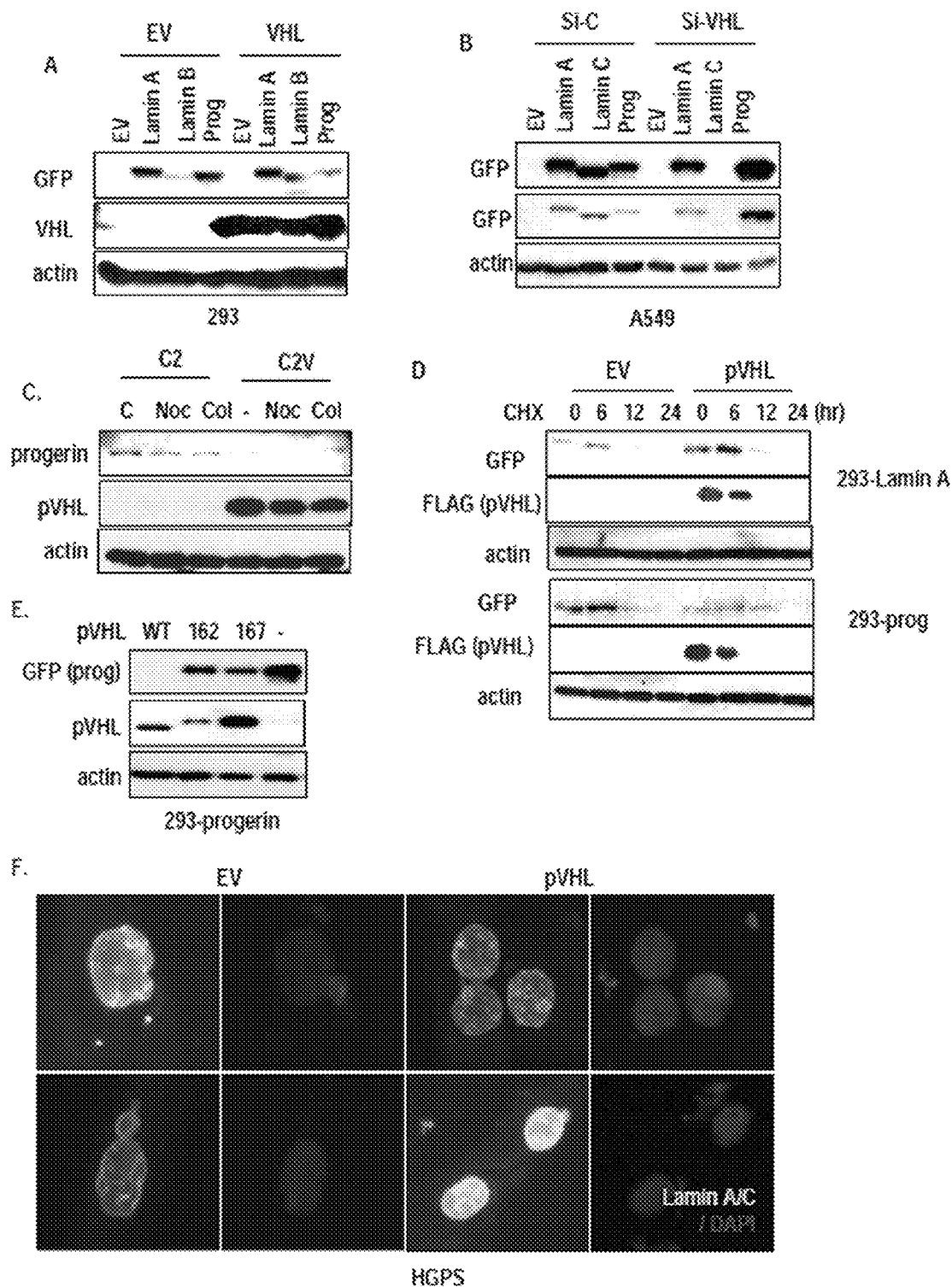
FIG. 2 demonstrates the suppression of pVHL against progerin expression in terms of the effect of pVHL overexpression on progerin expression (A), the effect of si-VHL on progerin expression (B), progerin level in pVHL-stably transfected C2V cells (C), the effect of pVHL mutations on progerin expression (D), the effect of pVHL mutants on progerin expression (E), and the effect of pVHL on the nuclear deformation of HGPS cells (F).

As previously stated, pVHL blocks the progerin expression (FIG. 2). Thus, the effect of pVHL on the p53 expression in RCC was examined. The forced expression of pVHL restored the reactivity of p53 to a DNA damaging agent as well as the MDM2 inhibitor nutlin-3 in C2 and caki-2 cell lines (FIGS. 4A and 4B). In fact, p53 was expressed at a higher level in C2V than in the C2 cell line under a non-stimulated condition.

A report has it that pVHL can activate p53 through direct interaction. The effect of pVHL was examined in the progerin-negative cell lines, HCT116 and A549. In these cell lines, however, neither a significant induction of p53 nor a synergic effect with DNA damaging agents was not observed (FIGS. 4C and 4D). This result indicates that pVHL-mediated p53 induction is achieved by the suppression of progerin.

Moreover, co-transfection of si-progerin and pVHL enhanced the p53 expression in a synergistic manner (FIG.

Figure 11:
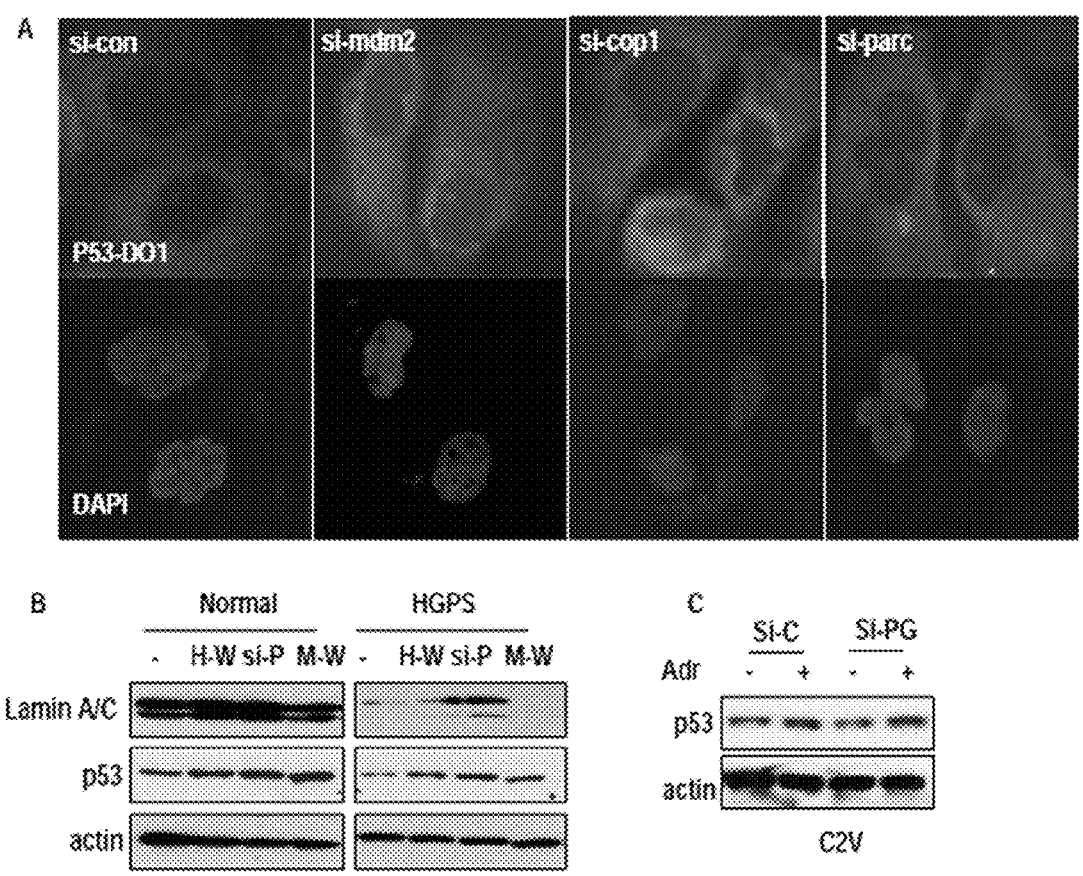
FIG. 11 demonstrates the induction of p53 by si-progerin in a progerin-dependent manner in terms of the immunostaining assay of p53 in C2 cells (A), the effect of si-progerin on p53 induction in HGPS cells (B), and the effect of si-progerin on p53 induction in C2V cells (C).

4E). However, neither the induction of p53 nor the enhancement of p53 responsibility to DNA damage in C2V by si-progerin was observed (FIG. 11C). These results suggest that p53 inactivation in RCC would result from an elevated expression of progerin, which could be gained by pVHL defect.

An examination was also made of p53 expression in si-progerin- or pVHL-transfected HGPS cells. In both the conditions, progerin was commonly reduced while p53 was increased (FIGS. 4F and 4G).

Taken together, the results imply that pVHL11-mediated p53 activation would be achieved by progerin suppression.

5) Progerin Blocks p14-Mediated p53 Activation.

Figure 5:
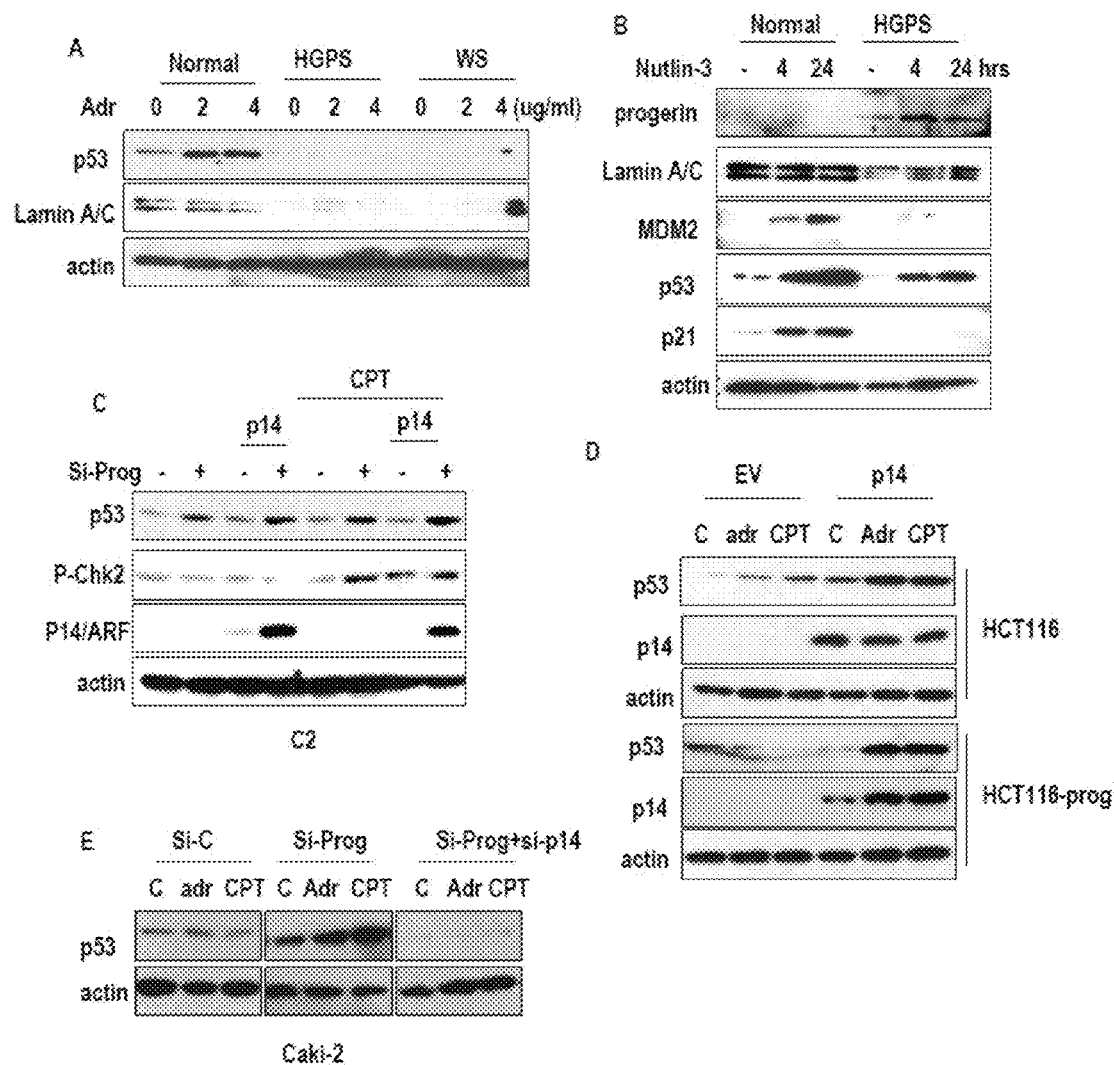
FIG. 5 demonstrates the inhibitory activity of progerin against p14-mediated p53 activation in terms of the insensitivity of p53 in human progeroid cells (A), the effect of Nutlin-3 on p53 induction in HGPS cells (B), the effect of si-progerin on DNA damage response in C2 cells (C), the effect of p14 overexpression on progerin-induced p53 suppression (D), and the effect of si-p14 on p53 induction (E).

The molecular mechanism of the inhibitory activity of progerin against p53 was scrutinized and p53 responsibility to DNA damage was determined in human progeria cell lines (HGPS and WS). Compared to normal cells where p53 was obviously increased by Adr, HGPS and Werner syndrome (WS) cells did not show the induction of p53 (FIG. 5A). WS cells are known to be insensitive to DNA damage-induced p53 activation, and as previously observed, WS cells can also express progerin. This result implies that progerin can block the DNA damage-induced p53 activation pathway.

Keeping in mind the fact that p53 is tightly regulated by the MDM2 pathway, the engagement of progerin with MDM2-mediated p53 suppression was also tested by treatment of Nutlin-3, which is a blocker between MDM2 and p53 and induces p53 expression. This chemical induced p53 obviously in normal cells (FIG. 4B), but elicited a partial response in HGPS cells (FIG. 5B). Moreover, nultlin-3 did not induce p53 obviously in C2 and Caki-2 cell lines (FIG. 4B). Considering the results, the elevated expression of progerin would be involved in DNA damage-induced p53 activation and MDM2-mediaeted p53 suppression.

Figure 12:
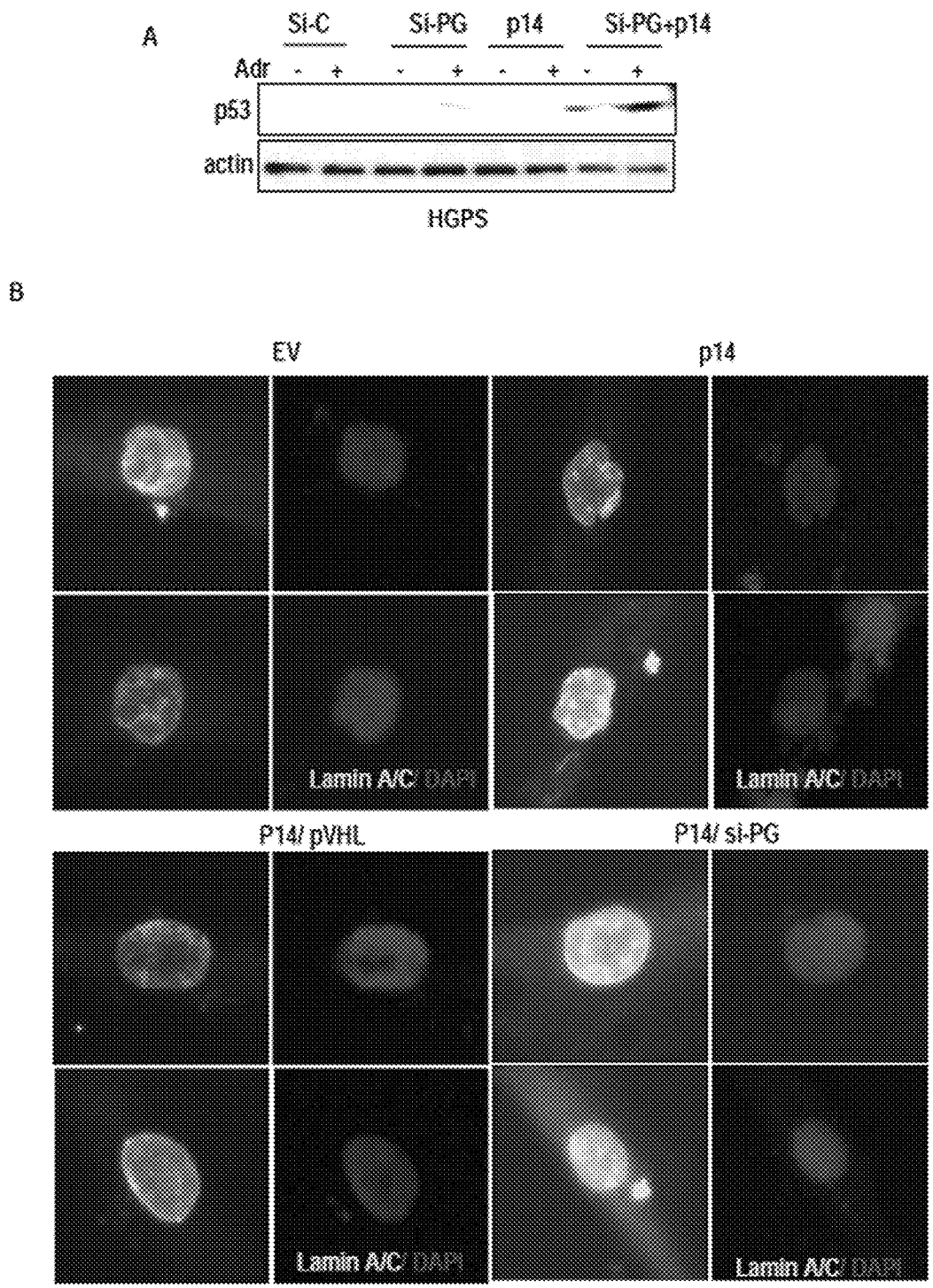
FIG. 12 demonstrates the regulation of p14 by progerin in terms of the synergic effect of p14 and si-progerin (Si-PG) (A), and the effect of P14 on nuclear morphology (B).

Since p14/ARF is an inhibitor against MDM2 and is activated by ATM/ATR-dependent DNA damage signaling, it had risen as a strong candidate for the missing link of progerin-mediated p53 suppression. To elucidate this, p53 expression was determined by WB analysis following transfection with p14/ARF. As a result, DNA damage did not induce C2 cells to express p53. However, si-progerin re-stored the responsibility (FIG. 5C). Moreover, si-progerin increased the expression of p14/ARF (FIG. 5C). To confirm this, an examination was made of the expression of p53 in HGPS cell after transfection with si-progerin and p14. In this cell line, the elimination of progerin induced p53 expression in synergy with the overexpression of p14 (FIG. 12A).

With regard to the effect of p14 on progerin-induced p53 inactivation, p14/ARF enhanced the responsibility of p53 in HCT116 while progerin blocked the p53 activation (FIG. 5D). However, the forced expression of p14 overcame progerin-induced p53 suppression (FIG. 5D). It was also observed that si-progerin-induced p53 activation in Caki-2 was blocked by si-RNA against p14 (FIG. 5E). These results indicate that p14 would function downstream of progerin and progerin would block p53 activation through the suppression of p14.

Progerin can induce nuclear deformation. It was examined whether p14 had an influence on the nuclear deformation of HGPS. Although pVHL and si-progerin could reduce nuclear irregularity and deformation, p14 alone could not ameliorate nuclear deformation (FIG. 11B). This result implies that progerin-p14 interaction is restricted in p53 regulation, and that nuclear deformation or irregularity would result from the elevated expression of progerin.

6) pVHL Blocks Interaction Between Progerin and p14.

Figure 6:
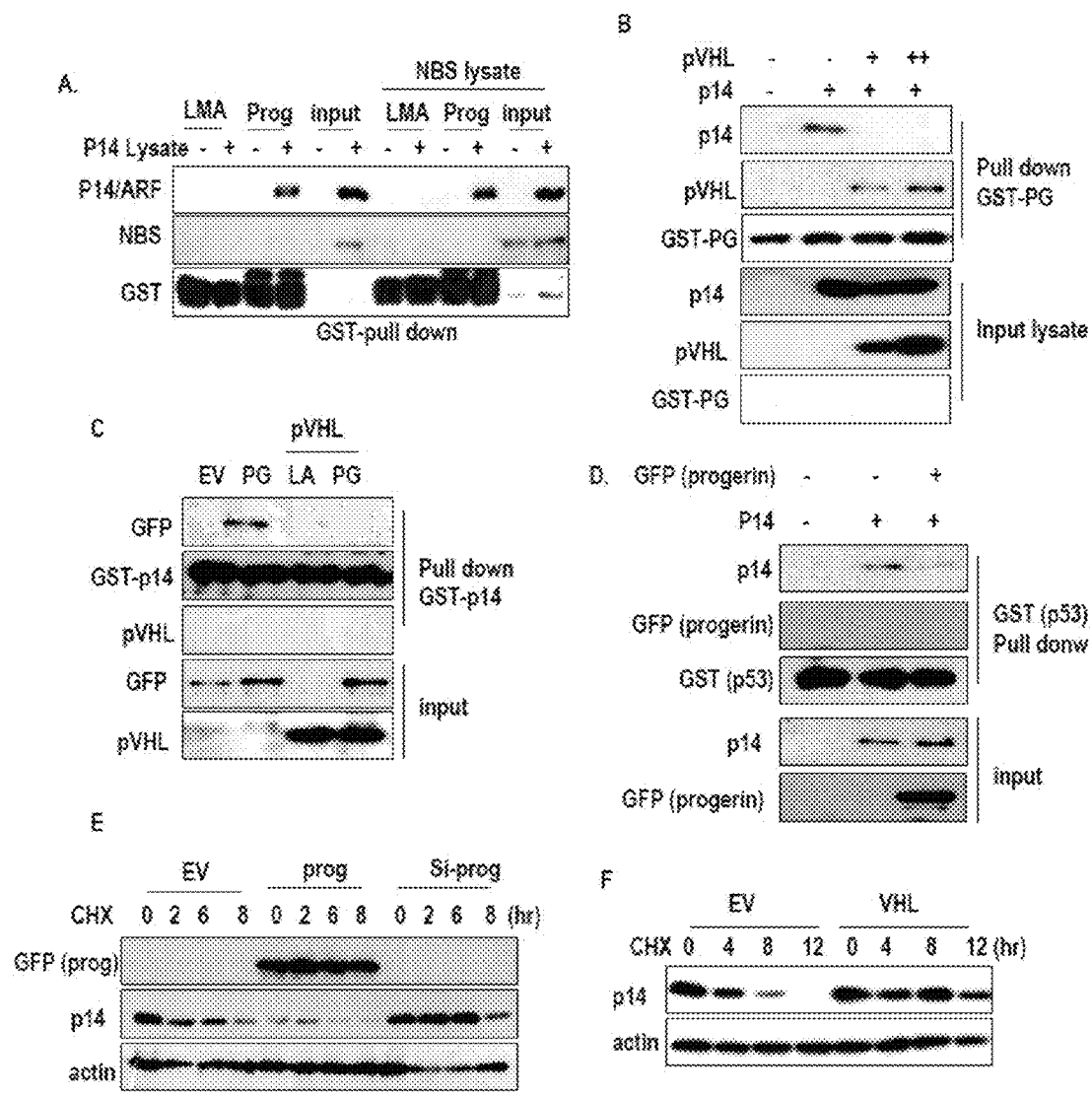
FIG. 6 demonstrate the inhibitory activity of pVHL against direct interaction between p14 and progerin in terms of interaction between p14 and progerin (A), the effect of pVHL on interaction between p14 and progerin (B), a GST-pull down assay using GST-p14 (C), the effect of progerin on interaction between p53 and p14 (D), the effect of progerin on the half-life of p14 (E), and the effect of pVHL on the half life of p14 (F).

To know how progerin blocks the p14 function, interaction between progerin and p14 was monitored through GST pull down assay. p14 was found to specifically interact with progerin, but not with Lamin A (FIG. 6A). To confirm the specific interaction between p14 and progerin, an NBS-transfected cell lysate was added. However, NBS protein interacted with neither progerin nor Lamin A (FIG. 6A). In contrast, the addition of pVHL-cell lysate blocked the binding of p14-progerin (FIG. 6B).

To avoid artifacts, interaction with GST-p14 was also examined. Consistent with a previous result, GST-p14 exhibited specific binding with progerin (FIG. 6C). In addition, pVHL blocked interaction between GST-p14 and progerin. However, pVHL was not associated with p14-GST protein (FIG. 6C).

Supporting the pervious result that pVHL binds progerin and blocks p14, this data suggests the interruption of pVHL against p14-progerin interaction. Thus, in pVHL-deficient cells such as RCC, progerin may be more likely to bind p14 to inactivate p53. To confirm this, the effect of progerin on p14-p53 association was checked. Interaction between p53-p14 was disrupted by progerin (FIG. 6D). When these data are taken into consideration, an elevated level of progerin in a pVHL-deficient condition is suggested to block p14, causing the inactivation of p53. Next, p14 was examined for protein stability since the elimination of progerin induces p14 expression (FIG. 5C). Progerin was found to reduce the half life of p14 whereas si-progerin could extend it, as measured by the pulse-chase analysis (FIG. 6E). Also, a prolonged half-life of p14 was observed in pVHL-transfected cells (FIG. 6F). These results suggest that pVHL can extend the half-life of p14 through the suppression of progerin.

7) The Expression of Progerin is Elevated in Human Leukemia

Since progerin can suppress p53 through p14 inactivation, it is assumed that other kinds of cancers also show an elevated expression of progerin. To test this, the expression of progerin was examined in 16 leukemia and 3 normal blood samples. As previously reported, leukemia shows resistance to chemo- and radiation therapy and pleomorphic nuclei. Half of the 19 samples expressed progerin (FIG. 7A), with no progerin expression in the normal samples. No differences between acute myeloid leukemia and acute lymphatic leukemia were detected (Table 1).

TABLE 1

| | | | | | Expression Level | |
| --- | --- | --- | --- | --- | --- | --- |
| # | Age | Gender | Diagnosis | Description | Lamin A/C | Progerin |
| 1 | 38 | M | AML-M1 | Acute myeloid leukemia without maturation, M1 | 5 | 5 |
| 2 | 57 | F | ALL-remission | Acute lymphoblastic leukemia in remission | 5 | 5 |

TABLE 1-continued

| # | Age | Gender | Diagnosis | Description | Lamin A/C | Progerin |
|---|---|---|---|---|---|---|
| 3 | 44 | F | AML-M1 | Acute myeloid leukemia without maturation, M1 (in regenerating marrow with engraftment. Allo SCT 14 days) | 5 | 5 |
| 4 | 29 | M | AML-M1 | Acute myeloid leukemia without maturation, M1 (in regeneration) | 5 | 5 |
| 5 | 21 | F | ALL | Acute lymphoblastic leukemia, B lymphoblastic leukemia (regenerating marrow without residual leukemia, f/u, Chemotherapy 21 days) | 5 | 5 |
| 6 | 72 | M | AML-M3 | Acute promyelocytic leukemia, microgranular type, M3 in recurrence | 5 | 5 |
| 7 | 38 | F | AML-M1 | Acute myeloid leukemia, without maturation, FAB(M1) in recurrence | 5 | 5 |
| 8 | 36 | M | AML-M1 | Acute myeloid leukemia without maturation (M1) in remission | 5 | 5 |
| 9 | 66 | F | AML-M1 | Acute myeloid leukemia without maturation (M1), with t(6:11), MLLT4-MLL, refer to RT-PCR | 5 | 5 |
| 10 | 72 | M | AML-M4 | Acute myelomonocytic leukemia in regenerating granulocytic hyperplasia with a few residual leukemic cells. f/u, chemotherapy 28 days | 5 | 5 |
| 11 | 29 | F | ALL-B | Acute lymphoblastic leukemia B lymphoblastic leukemia | 0 | 0 |
| 12 | 66 | M | AML-M4 | Acute myelomonocytic leukemia | 4 | 0 |
| 13 | 44 | F | AML-M1 | Acute myeloid leukemia without maturation, M1 | 5 | 0 |
| 14 | 41 | F | AML-M3 | Acute promyelocytic leukemia with PMLRARa | 2 | 0 |
| 15 | 37 | M | AML-M3 | Acute promyelocytic leukemia, microgranular | 0 | 0 |
| 16 | 57 | F | ALL-B | Acute lymphoblastic leukemia, B lymphoblastic leukemia (WHO) | 0 | 0 |
| 17 | 26 | M | Normal | Normocellular marrow without tumor involvement | 1 | 0 |
| 18 | 45 | F | Normal | Nomocellular marrow, otherwise not specific | 2 | 0 |
| 19 | 49 | M | Normal | Nomocellular marrow without myeloma involvement, f/u | 3 | 0 |

Figure 7:
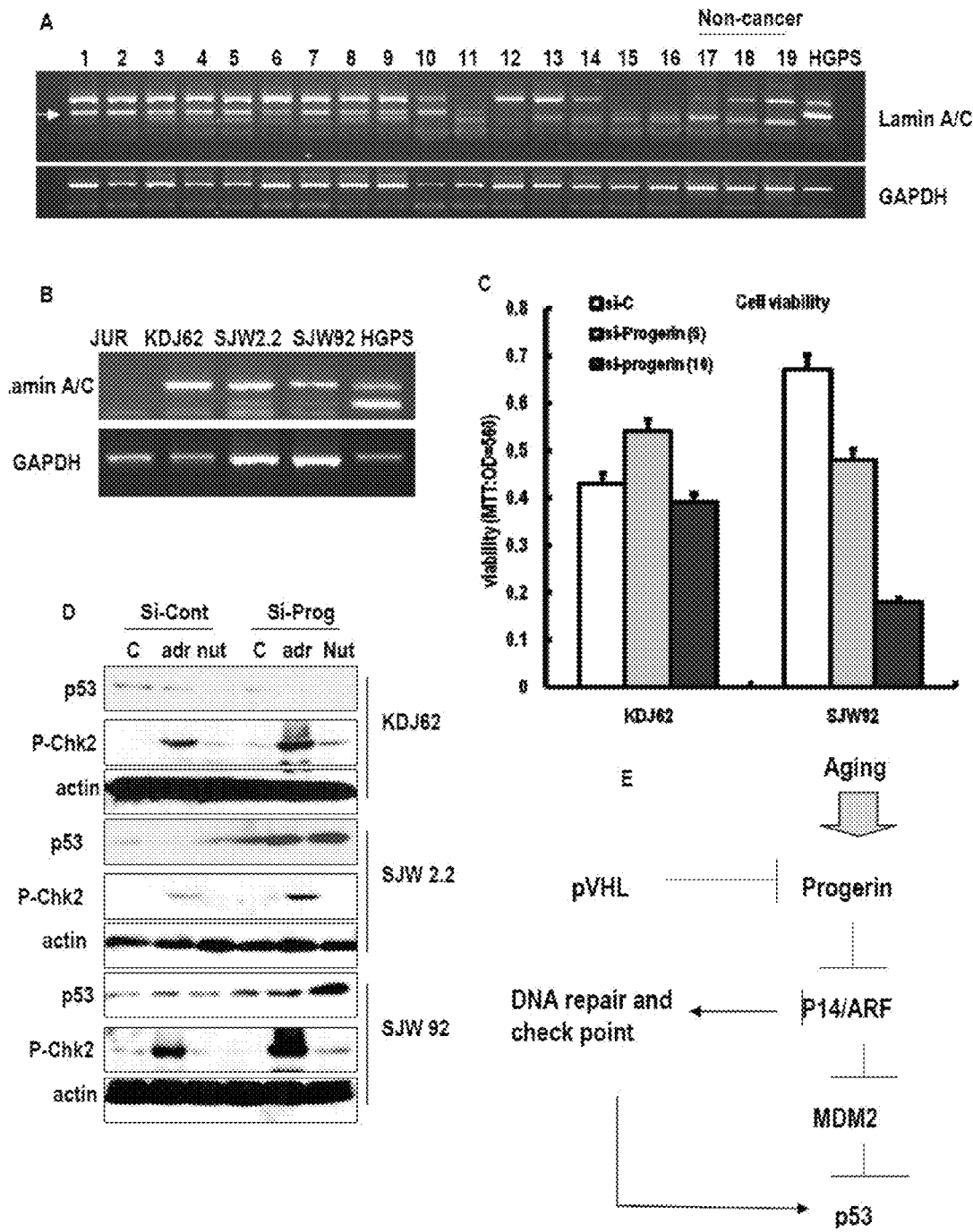
FIG. 7 demonstrated an elevated expression of progerin in human leukemia samples in terms of progerin expression in leukemia samples (A) and in established cell lines (B), cell viability in the presence of si-progerin (C), the effect of si-progerin on p53 expression and DNA damage response (D), and a mechanism of cancer progression according to senescence (F).

From these samples, 3 different leukemia cell lines (KDJ62, SJW2.2 and SJW 92) were established, and examined for progerin expression. Of them, SJW 2.2 and 92 allowed the expression of progerin (FIG. 7B). The data on cell viability examined after the elimination of progerin exhibited that SJW 92 was sensitive to si-progerin. However, KDJ62 did not respond to si-progerin (FIG. 7C). Also, the activation of p53 and response to DNA damage through p-chk2 were investigated in these cell lines. In KDJ 62, si-progerin did not induce p53 activation and p-Chk2 in response to adriamycin and Nutlin-3. In contrast, SJW2.2 and 92 showed a response to si-progerin (FIG. 7D).

These results suggest that SJW 92 and 2.2 lean to progerin-dependent p53 inactivation, like RCC. Hence, various kinds of cancers including RCC, leukemia and prostate cancer would overcome p53-induced tumor suppression through progerin overexpression, which blocks the p14-induced p53 activation and DNA damage signaling (FIG. 7E).

Example 2

Senescence-Inhibiting Mechanism by Interaction Between Progerin and Lamin A

1. Cell Cultures and Reagents

Some of the cell lines used in the present invention (293; DMEM, A549, HCT116; RPMI-1640) were obtained from ATCC. The other cell lines (UMRC2; C2, UMRC2V; C2V, CAKI2; DMEM) were granted from Dr. Jung Y J (Pusan National University). Stable cell lines were established by introducing GFP-fused Lamin A or progerin vector into HEK293 cells. Selection for the stable cell lines was made in the presence of 6418 (200 μg/ml). All the cell lines were maintained at 37° C. in broth containing 10% FBS and 1% antibiotics in a growth chamber.

Human fibroblast cells from HGPS patients (AG01972; 14-years-old female, AG03513; 15-years-old male), an ataxia telangiectasia patient (ATM; AG04405, 6-years-old male), and a normal person (GM 00038; 9-years-old female) were obtained from the Coriell Cell Repositories, and were maintained in EMEM, containing 15% FBS and 2 mM Glu without antibiotics.

Also, a purchase was made of general chemical inhibitors including FTI (FTI-277), GGTI (GGTI-298) and colcemide from Sigma-Aldrich, and various antibodies against progerin (sc-81611), Lamin A/C (sc-20680), Lamin B (sc-6216), GST (sc-138), GFP (sc-9996), p53 (DO-1) (sc-126), actin (sc-1616), p16 (sc-759), DcR2 (sc-65310), His (sc-8036), and DNA-PKcs (sc-9051) from Santa Cruz, an antibody against H3k9Me3 (ab-8858) from Abcam, and an antibody against p14/ARF (MS-850-P0) and Emerin from Novocastra.

2. Vectors and Transfection

GFP-fused progerin and GFP-fused Lamin A expression vectors were kindly provided by Scaffidi and Misteli (NCI). GRP-fused Lamin B and Lamin C were granted from Lammerding J (Brigham and Women's Hospital/Harvard Medical School). A mutant of Lamin A was granted from Tesson F (University of Ottawa). A Myc-ARF vector and a non-tagged progerin vector were purchased from Addgene. For mammalian expression of these vectors, transfection was performed with the aid of Jetpei (Polyplus). In 150 nM NaCl solution, 1.5 µg of each vector was mixed with 1.5 µl of the Jetpei reagent. After incubation for 15 min at room temperature, the mixture was added to the cells. After 3 hrs, the 10% FBS medium was replaced by a serum-free medium.

3. Recombinant Proteins and GST-Pull Down

For use in protein-protein interaction analysis, recombinant proteins were prepared. A Lamin A-N-terminal region was obtained as a stretch of 300 amino acids downstream of the initiation codon while a Lamin A-C-terminal region (L-C), and a progerin-C-terminal region (Prog) were amplified from 100 amino acids upstream of respective termination codons by PCR. Full-length p14 was also obtained by PCR and cloned into a pGEX vector before confirmation by base sequencing. Using a nickel column, these recombinant proteins were purified. For the binding assay, GST-bead-fused Lamin A-C or progerin-C was incubated for 2 hrs at room temperature with a lysate of 293 cells transfected with the lamin A-N terminal region, or GFP-Lamin A, B or C. After washing twice with PBS and once with RIPA, the precipitates were collected, and subjected into SDS-PAGE and Western blot analysis with anti-GFP, His, and GST antibodies.

4. Immunoprecipitation (IP) and Western Blot (WB) Analysis

Whole cell lysates were prepared in RIPA buffer, and centrifuged at 14,000 rpm for 30 min. Twenty micrograms of cell extracts were separated by SDS-polyacrylamide gel electrophoresis and transferred onto a PVDF membrane. The membrane was incubated for 1 hr to overnight at 4° C. with an appropriated primary antibody, followed by reaction with a secondary antibody at room temperature for 1 hr. Peroxidase activity was detected by chemiluminescence with an ECL kit (Intron) as recommended by the manufacturer.

To examine interaction between Lamin A and progerin, the protein extracts were added with an antibody against GFP (2 g/sample). After incubation for 2 hrs at 4° C. with agitation, protein A and protein G were added. After washing twice with PBS, the precipitates were dissolved in RIPA buffer and SDS sample buffer.

5. Immunofluorescence Staining and Senescence-Specific Acidic-Galacosidase Activity Staining Cells transfected with predetermined vectors were fixed with 100% methanol for 10 min at 4° C. on cover glass. After washing with PBS, the cells were incubated in a blocking buffer (PBS+anti-human Ab (1:500)) for 1 hr. Then, the cells were washed twice with PBS, and incubated with an anti-Lamin A/C H3K9Me3, or DNA-PKcs antibody in a blocking buffer (1; 200) for 2 hr and sequentially with an anti-goat Ab-FITC or anti-Rabbit ab-Rhodamin in a blocking buffer (1:1000) for 2 hr. The cells were mounted on a slide, and stained for nuclei with DAPI. Immunofluorescence signals were detected by fluorescence microscopy (Zeiss).

For senescence-specific acidic-β-galactosidase activity staining, cells were washed once with PBS (pH 7.2) and fixed with PBS containing 0.5% glutaraldehyde. After being washed with PBS, the cells were stained overnight at 37° C. in an X-gal solution (Senescence β-Galactosidase Staining kit; Cell Signaling Technology).

6. RNA isolation and RT-PCR

For RT-PCR, total cellular RNA was extracted using a Qiagen RNA extraction kit. After measurement of RNA concentration, 1 µg of total RNA was reverse transcribed to cDNA using random hexamers in the presence of MMLV RT (Invitrogen). RT-PCR was performed with the following specific primers:

```
Lamin A/C Forward:
5'- AAGGAGATGACCTGCTCCATC -3'      (SEQ ID NO: 1)

Reverse:
5'- TTTCTTTGGCTTCAAGCCCCC-3'       (SEQ ID NO: 2)

GAPDH Forward:
5'-ATCTTCCAGGAGCGAGATCCC-3'        (SEQ ID NO: 3)

Reverse:
5'-AGTGAGCTTCCCGTTCAGCTC-3'.       (SEQ ID NO: 4)
```

7. MTT Assay and Cell Proliferation

To measure cell viability, cells were treated with predetermined binding inhibitors of the present invention for 24 hrs. For MTT assay, the cells were incubated with a 0.5 mg/ml MTT solution for 4 hr at 37° C. Excess solutions were removed, and the precipitates were dissolved in 200 µl of DMSO and quantified by reading absorbance at 540 nm.

For cell counting, cells were harvested from media, and stained for 10 min at room temperature with Trypan blue. Viable cells were counted using a hemocytometer.

8. ELISA

To isolate a Lamin A-Prg binding inhibitor, ELISA analysis was carried out. GST-progerin-C or LMNA-His was fixed with 0.5% paraformaldehyde on 96-well plates. After drying and washing steps, lysates of HEK 293 cells transfected with GFP-Lamin A, GST-Lamin A-C, or GST-progerin-C were incubated for 1 hr with a 0.1 mM (final concentration) binding inhibitor of the present invention. The 96-well plates were washed with TBST, followed by reaction with an anti-GFP-Ab (1:10,000, 45 min), an anti-GST-Ab (1:10,000, 45 min) and an anti-mouse-IgG-HRP (1:50,000, 30 min). The plates were washed twice, and incubated with a TMB solution (Calbiochem) and then with a stop solution (1 N $H_2SO_4$). Absorbance was read on an ELISA reader.

9. In Vivo Assay

C57Bl/6J mice (n=28) were divided into four groups, and intraperitoneally injected once a week for six weeks with DMSO or a JH compound according to one embodiment of the present invention at a dose of 20 mg/kg. Experiments were performed properly according to the rule of the "Association for Assessment and Accreditation of Laboratory Animal Care of Pusan University.

10. Results

1) Progerin Causes Senescence Through Binding to LMN A.

Figure 13:
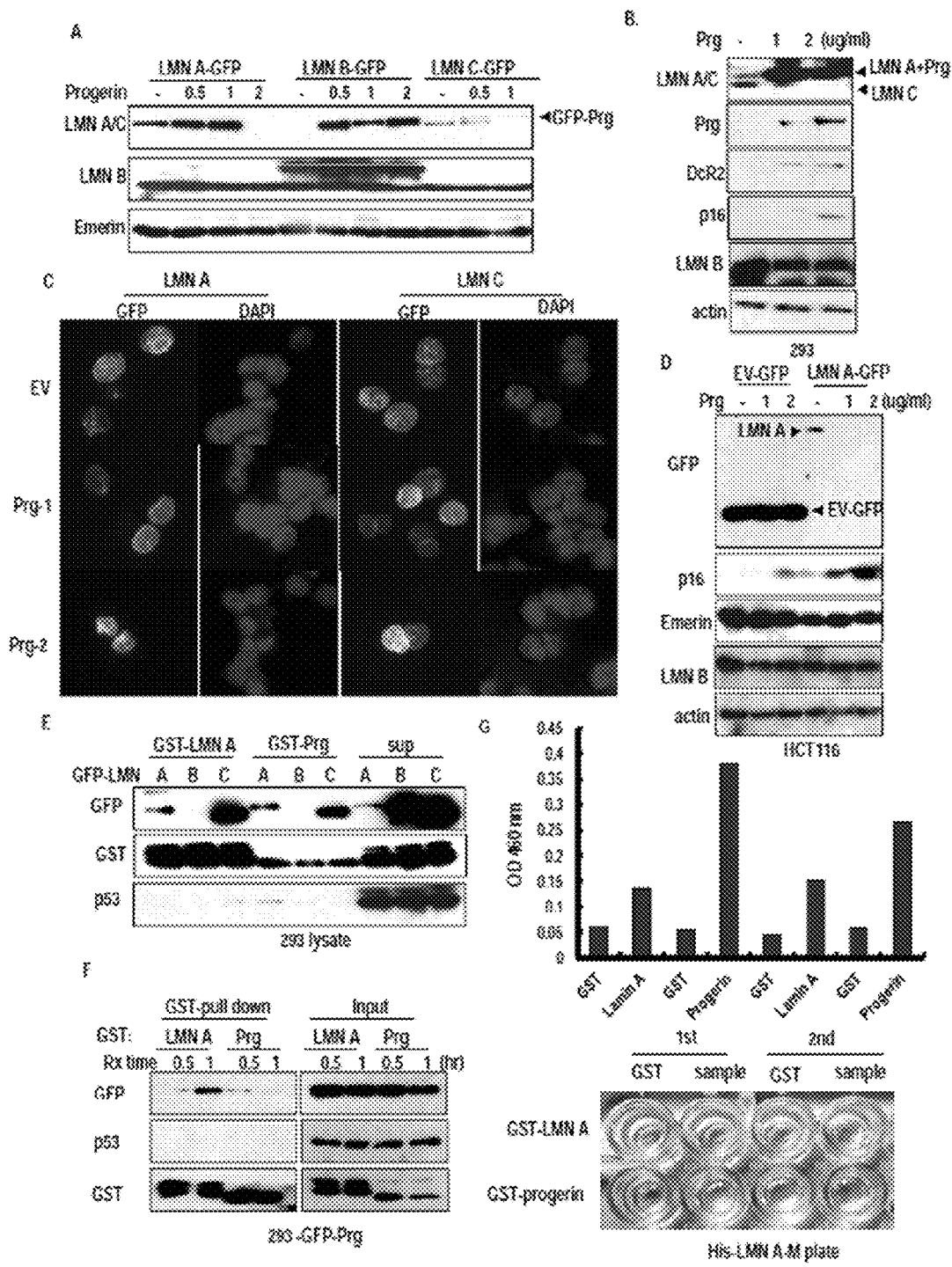
FIG. 13 shows direct interaction between progerin and Lamin A/C (LMN A/C), and the effect thereof, as obtained in Example 2-10-1.
Figure 14:
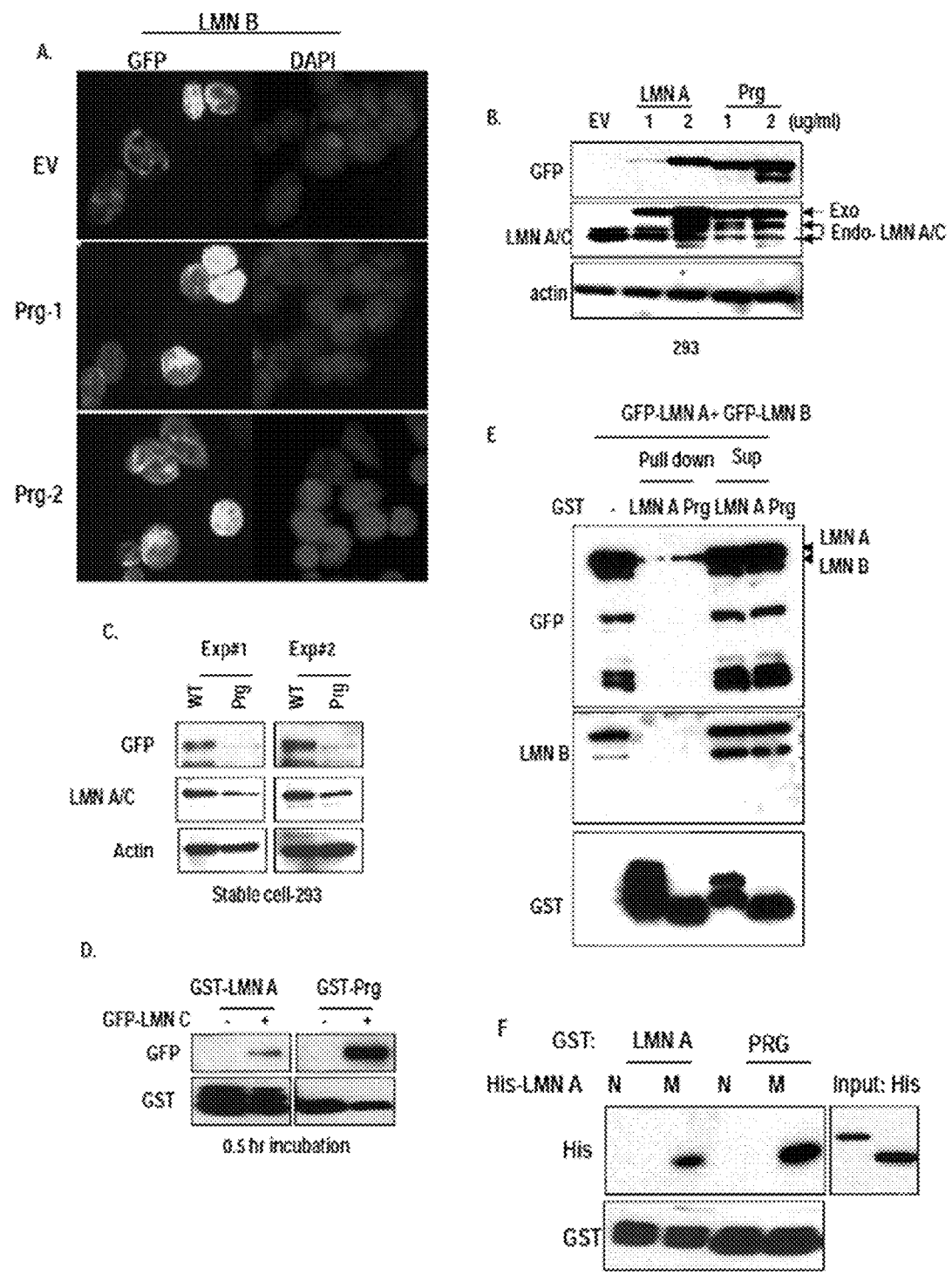
FIG. 14 shows that progerin binds to Lamin A/C, but does not to Lamin B, as obtained in Example 2-10-1.

As phenotypes of HGPS are determined by progerin expression, an examination was made of the effect of progerin on the Lamin family. Co-transfection of GFP-LMN A/B/C and GFP-progerin suppressed LMN A/C expression, but not LMN B expression (FIGS. 13A and 14A). The effect of Prg on endogenous LMN A/C was determined by analyzing LMN A/C expression in non-tagged and GFP-Prg transfected cells. Consistent with the previous results, progerin suppressed LMN A/C (FIGS. 13B and 14B). In addition, progerin expression can induce general senescence markers including p16 and DcR2 (FIG. 13B), and nuclear deformation, a typical feature of HGPS (FIG. 13C). To confirm the reduction of LMN A by progerin, the effect of Prg on LMN A expression was measured again in HCT116 and Prg-stable cells. In both cases, a reduction of LMN A/C was detected in progerin-transfected cells (FIGS. 13D and 14C).

To address how progerin regulates LMN A/C, a binding assay was performed. As a result, a C-terminal region of progerin and LMN A were found to associate with LMN A/C, but not with LMN B (FIG. 13E). Progerin showed stronger binding affinity to LMN A/C than LMN A (FIGS. 14D and 14E). In contrast, progerin did not form a self-associate (FIG. 13F).

For use in searching into the binding domain, a His-tagged LMN A N-terminal region (LMN A-N; 1-300 AA) and an LMN A middle region (LMN A-M; 301-564 AA) were constructed. A GST-pull down assay was carried out with GST-LMN A or GST-progerin. From this experiment, it was found that the middle region of LMN A was responsible for binding with progerin (FIG. 14F).

To quantify the binding affinity, an ELISA system comprising immobilized LMN A-M terminal domain, and GST-fused recombinant LMN A or Prg protein was established. An ELISA analysis revealed that binding affinity between LMN A and progerin was twice as strong as the self-association of LMN A (FIG. 13G).

2) Screening of Inhibitors Against Binding Between Progerin and Lamin A

Figure 15:
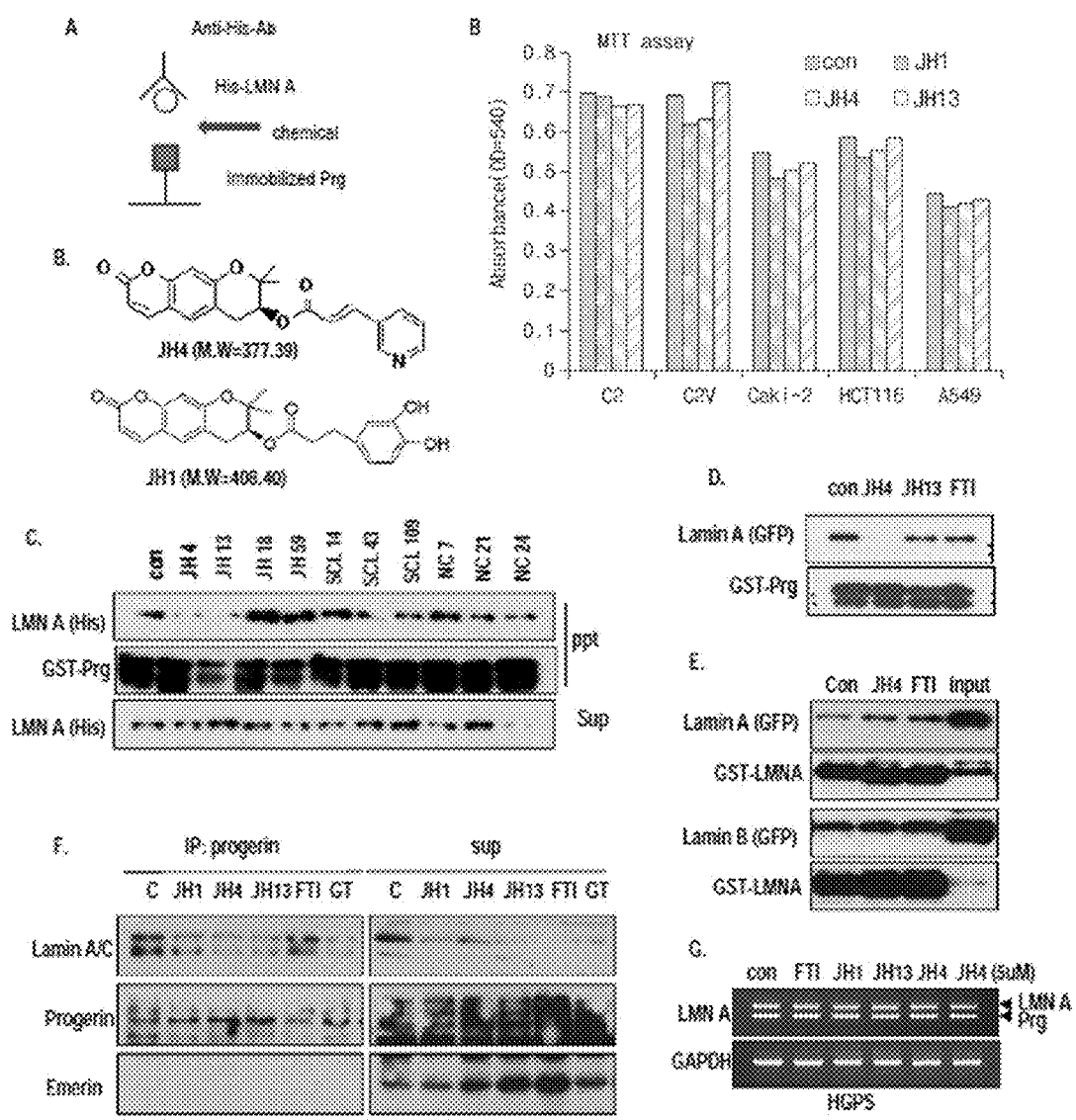
FIGS. 15 and 16 show screening procedures and results of progein inhibitors, as carried out in Examples 2-10-2 and 2-10-3.
Figure 16:
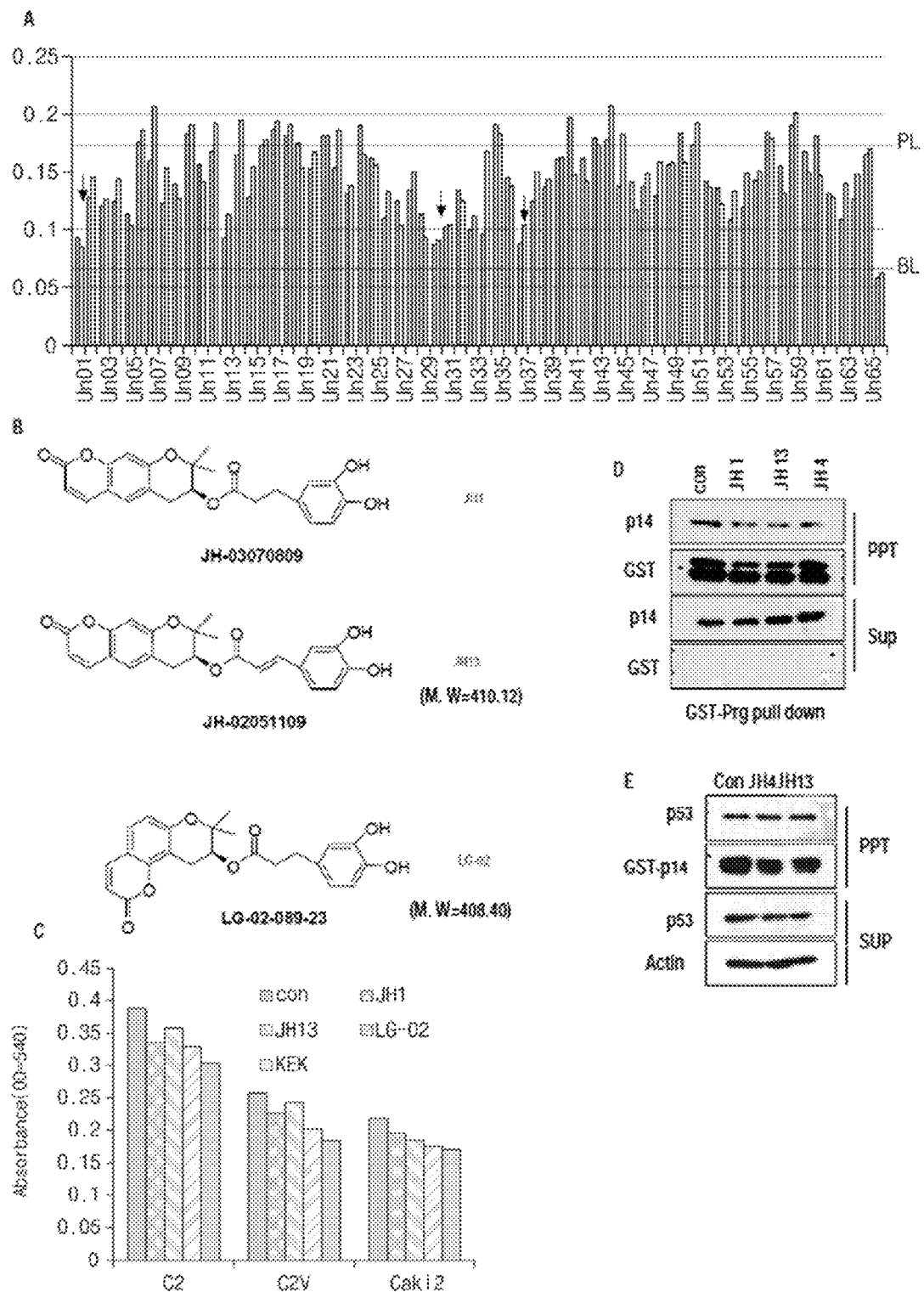

If progerin-induced senescence is mediated by binding LMN A, an inhibitor against binding between LMN A and progerin would block the progerin-induced pathological features. For use in demonstrating this hypothesis, LMN A-Prg binding inhibitors were excavated. In this regard, an ELISA-based screening system was established. Briefly, progerin immobilized in 96-well plates was incubated with candidates from a chemical library, together with GFP-LMN A. Subsequently, association between progerin and the GFP protein was monitored in the presence of the inhibitor candidates (FIG. 15A). From the chemical library, four effective different compounds (JH-0307809; JH1, JH-02051109; JH13, JH-03070708; JH4, and LG-02-089-23; LG-02) were selected (FIGS. 15B and 16B), and analyzed by the monitoring (FIG. 16A). All of them were found to have similar chemical structures. Their cytotoxicity was evaluated by MTT assay (FIGS. 15B and 16C).

3) Synthesis of the Candidates and NMR Data

The compounds JH1, JH4, JH13, and LG-02 were synthesized as illustrated in the following Reaction Schemes 1 and 2:

[Reaction Scheme 1]

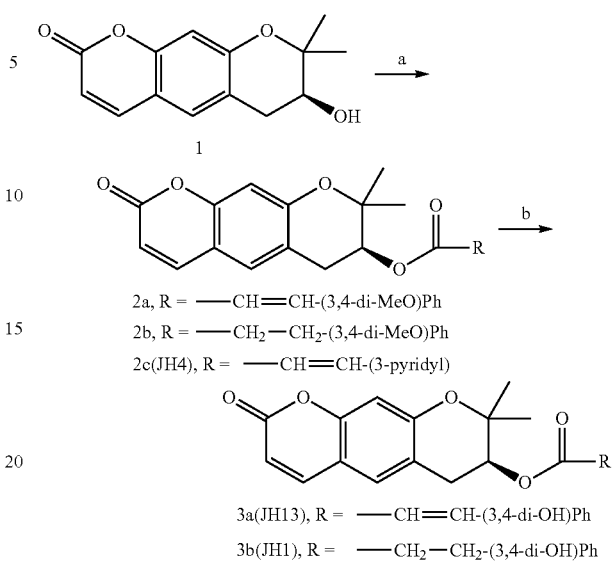

2a, R = —CH=CH-(3,4-di-MeO)Ph
2b, R = —CH$_2$—CH$_2$-(3,4-di-MeO)Ph
2c(JH4), R = —CH=CH-(3-pyridyl)

3a(JH13), R = —CH=CH-(3,4-di-OH)Ph
3b(JH1), R = —CH$_2$—CH$_2$-(3,4-di-OH)Ph

Reagents and conditions: (a) carboxylic acid, EDC, 4-DMAP, dry dichloromethane, 5-12 hrs, room temperature; (b) 1 M BBr$_3$ in dichloromethane, dry dichloromethane, 0° C.→room temperature, 5 hrs.

[Reaction Scheme 2]

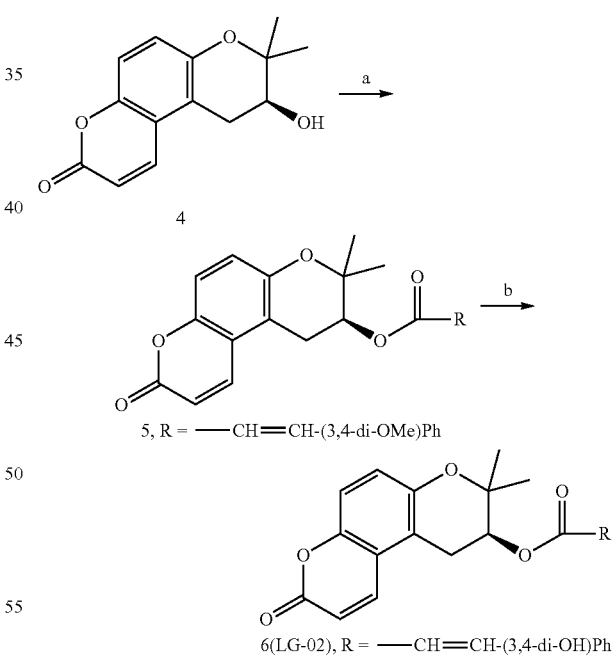

5, R = —CH=CH-(3,4-di-OMe)Ph

6(LG-02), R = —CH=CH-(3,4-di-OH)Ph

Reagents and conditions: (a) carboxylic acid, EDC, 4-DMAP, dry dichloromethane, 12 hrs, room temperature; (b) 1 M BBr$_3$ solution in dichloromethane, dry dichloromethane, 0° C.→room temperature, 5 hrs.

A. Synthesis of JH13 and JH1

A (S)-(+)-decursinol solution (1, 0.406 mmol, 1 eq) in dry dichloromethane was added to a mixture of an appropriate carboxylic acid (0.609 mmol, 1.5 eq), N-(3-dimethylaminopropyl)-N'-ethylcarbodiimide hydrochloride (EDC, 0.812 mmol, 2 eq) and 4-(dimethylamino)pyridine (4-DMAP, 0.162 mmol, 0.4 eq), followed by stirring for 5-12 hrs at room temperature. Subsequently, the reaction mixture was concentrated at a reduced pressure, and the concentrate was purified by silica gel chromatography to give a decursin derivative (2a, b). A solution of the decursin derivative having 3,4-dimethoxyphenyl (2a or 2b, 0.49 mmol, 1 eq) in dry dichloromethane (5 ml) was added to a 1 M boron tribromide solution (1.47 mmol, 3 eq) in dichloromethane in an ice bath. The resulting mixture was stirred at room temperature for 5 hrs. Purification was performed by silica gel short-column chromatography to afford decursin derivatives having a 3,4-dihydroxyphenyl group (3a; JH13, 3b; JH1).

3a: Compound JH13 [(7S)-(+)-3-(3,4-Dihydroxy-phenyl)-acrylic acid, 8,8-dimethyl-2-oxo-6,7-dihydro-2H,8H-pyrano[3,2-g]chromen-7-yl-ester)] was obtained as a white solid at a yield of 93.2%. Its data are as follows.

mp: 115° C., $R_f$=0.36 (1:2 n-hexane-ethyl acetate); [α]25 D +19.3 (c=3, CHCl$_3$); $^1$H NMR (400 MHz, DMSO-d$_6$): δ$_H$ 9.63 (1H, s OH-7'), 9.10 (1H, s, OH-6'), 7.90 (1H, d, J=9.6 Hz, H-4), 7.46 (1H, s, H-5), 7.45 (1H, d, J=15.2 Hz, H-3'), 7.00 (1H, s, H-5'), 6.99 (1H, d, J=8.4 Hz, H-9'), 6.81 (1H, s, H-10), 6.71 (1H, d, J=8.4 Hz, H-8'), 6.25 (1H, d, J=9.6 Hz, H-3), 6.22 (1H, d, J=15.6 Hz, H-2'), 5.14 (1H, t, J=4.0 Hz, H-7), 3.24 (1H, dd, J=4.0, 17.6 Hz, H-6a), 2.88 (1H, dd, J=4.0, 17.6 Hz, H-6b), 1.35 (3H, s, CH$_3$-8), 1.31 (3H, s, CH$_3$-8); $^{13}$C NMR (100 MHz, CDCl$_3$): δ$_C$ 166.9 (C-1'), 162.3 (C-2), 156.6 (C-9a), 154.0 (C-10a), 147.0 (C-7'), 146.2 (C-6'), 144.2 (C-3'), 143.9 (C-4), 128.8 (C-5), 126.8 (C-4'), 122.5 (C-9'), 116.0 (C-5a), 115.3 (C-8'), 114.3 (C-2'), 114.1 (C-3), 112.8 (C-4a), 112.7 (C-5'), 104.7 (C-10), 76.8 (C-8), 70.0 (C-7), 27.8 (C-6), 24.8 (CH$_3$-8), 23.3 (CH$_3$-8); IT-TOF/MS: m/z=409.1357 [M+H]$^+$, 431.1134 [M+Na]$^+$.

3b: Compound JH1 [(7S)-(+)-3-(3,4-Dihydroxyphenyl) propionic acid, 8,8-dimethyl-2-oxo-6,7-dihydro-2H,8H-pyrano[3,2-g]chromen-7-yl-ester] was obtained as a brown solid at a yield of 86.6%. Its data are as follows.

mp: 87° C., $R_f$=0.21 (1:1 n-hexane-ethyl acetate); [α]25 D+56.6 (c=1, MeOH); $^1$H NMR (400 MHz, DMSO-d$_6$): δ$_H$ 8.69 (1H, s, OH), 8.63 (1H, s, OH), 7.89 (1H, d, J=9.6 Hz, H-4), 7.39 (1H, s, H-5), 6.76 (1H, s, H-10), 6.54 (1H, d, J=8.0 Hz, H-9'), 6.509 (1H, s, H-5'), 6.34 (1H, d, J=8.4 Hz, H-8'), 6.24 (1H, d, J=9.6 Hz, H-3), 5.00 (1H, t, J=4.2 Hz, H-7), 3.14 (1H, dd, J=4.4, 17.6 Hz, H-6), 2.70 (1H, dd, J=4.8, 17.6 Hz, H-6), 2.61 (2H, t, J=7.2 Hz, H-3'), 2.490 (2H, t, J=7.2 Hz, H-2'), 1.23 (3H, s, CH$_3$-8), 1.22 (3H, s, CH$_3$-8); $^{13}$C NMR (100 MHz, DMSO-d$_6$): δ$_C$ 171.8 (C-1'), 160.2 (C-2), 155.7 (C-9a), 153.5 (C-10a), 144.9 (C-7'), 144.1 (C-6'), 143.8 (C-4), 130.9 (C-5), 129.5 (C-4'), 118.7 (C-5a), 115.7 (C-9'), 115.5 (C-5'), 115.3 (C-8'), 112.7 (C-4a), 112.5 (C-3), 103.4 (C-10), 76.5 (C-8), 69.3 (C-7), 35.4 (C-2'), 29.7 (C-3'), 27.0 (C-6), 24.3 (CH$_3$-8), 23.2 (CH$_3$-8); IT-TOF/MS: m/z=411.1393 [M+H]$^+$, 433.1283 [M+Na]$^+$.

B. Synthesis of JH4

A (S)-(+)-decursinol solution (1, 0.406 mmol, 1 eq) in dry dichloromethane was added to a mixture of trans-3-(3-pyridyl)acrylic acid (0.609 mmol, 1.5 eq), N-(3-dimethylaminopropyl)-N'-ethylcarbodiimide hydrochloride (EDC, 0.812 mmol, 2 eq) and 4-(dimethylamino)pyridine (4-DMAP, 0.162 mmol, 0.4 eq), followed by stirring for 12 hrs at room temperature. Subsequently, the reaction mixture was concentrated at a reduced pressure, and the concentrate was purified using silica gel column chromatography to give a decursin derivative (2c, JH4).

2c: Compound JH4 [(7S)-(+)-3-(3-Pyridyl)-acrylic acid, 8,8-dimethyl-2-oxo-6,7-dihydro-2H,8H-pyrano[3,2-g] chromen-7-yl-ester] was obtained as a white solid at a yield of 96.7%. Its data is given as follows.

mp: 105° C., $R_f$=0.24 (1:1 n-hexane-ethyl acetate); [α]20 D +48.5 (c=3, CHCl$_3$); $^1$H NMR (400 MHz, CDCl$_3$): δ$_H$ 8.72 (1H, d, J=2.2 Hz, H-5'), 8.60 (1H, dd, J=1.5, 4.9 Hz, H-7'), 7.81 (1H, d, J=8.4 Hz, H-9'), 7.67 (1H, d, J=16.0 Hz, H-3'), 7.58 (1H, d, J=9.6 Hz, H-4), 7.32 (1H, dd, J=4.8, 8.0 Hz, H-8'), 7.18 (1H, s, H-5), 6.83 (1H, s, H-10), 6.49 (1H, d, J=16.4 Hz, H-2'), 6.24 (1H, d, J=9.6 Hz, H-3), 5.21 (1H, t, J=4.8 Hz, H-7), 3.26 (1H, dd, J=4.8, 17.2 Hz, H-6a), 2.95 (1H, dd, J=4.8, 17.2 Hz, H-6b), 1.44 (3H, s, CH$_3$-8), 1.39 (3H, s, CH$_3$-8); $^{13}$C NMR (100 MHz, CDCl$_3$) δ$_C$ 165.6 (C-1'), 161.2 (C-2), 156.3 (C-9a), 154.2 (C-10a), 151.2 (C-5'), 149.8 (C-7'), 143.1 (C-4), 142.1 (C-3'), 134.2 (C-9'), 129.8 (C-4'), 128.7 (C-5), 123.7 (C-8'), 119.5 (C-2'), 115.5 (C-5a), 113.4 (C-3), 112.9 (C-4a), 104.8 (C-10), 76.5 (C-8), 70.5 (C-7), 27.8 (C-6), 24.9 (CH$_3$-8), 23.4 (CH$_3$-8 IT-TOF/MS: m/z=378.1325 [M+H]$^+$, 400.1129 [M+Na]$^+$.

C. Synthesis of LG-02

A (S)-(+)-coumarin solution (4, 0.406 mmol, 1 eq) in dry dichloromethane was added to a mixture of 3,4-dimethoxycinnamic acid (0.609 mmol, 1.5 eq), N-(3-dimethylaminopropyl)-N'-ethylcarbodiimide hydrochloride (EDC, 0.812 mmol, 2 eq) and 4-(dimethylamino)pyridine (4-DMAP, 0.162 mmol, 0.4 eq), followed by stirring for 12 hrs at room temperature. The reaction mixture was concentrated, and the concentrate was purified by silica gel column chromatography to give a coumarin derivative (5). A solution of the coumarin derivative having 3,4-dimethoxyphenyl (5, 0.49 mmol, 1 eq) in dry dichloromethane (5 ml) was added to a 1 M boron tribromide solution (1.47 mmol, 3 eq) in dichloromethane in an ice methane, and stirred at room temperature for 5 hrs. Purification was achieved by silica gel short-column chromatography to afford a coumarin derivative having a 3,4-dihydroxyphenyl group (6, LG-02).

6: Compound LG-02 [(6S)-(−)-3-(3,4-Dihydroxy-phenyl)-acrylic acid, 7,7-dimethyl-2-oxo-5,6-dihydro-7H-pyrano[3,2-f]chromen-6-yl-ester] was obtained as a white solid at a yield of 90.86%. Its data is given as follows.

mp: 117° C., $R_f$=0.15 (1:1 n-hexane-ethyl acetate); [α]20 D −140.82 (c=2, CHCl$_3$); $^1$H NMR (400 MHz, DMSO-d$_6$): δ$_H$ 9.63 (1H, s, 9.09 (1H, s, OH-6'), 8.09 (1H, d, J=9.6 Hz, H-4), 7.46 (1H, d, J=16.0 Hz, H-3'), 7.21 (1H, d, J=9.2 Hz, H-10), 7.09 (1H, d, J=9.2 Hz, H-9), 7.01 (1H, s, H-5'), 7.00 (1H, d, J=8.0 Hz, H-9'), 6.72 (1H, d, J=8.0 Hz, H-8'), 6.45 (1H, d, J=10.0 Hz, H-2'), 6.24 (1H, d, J=15.6 Hz, H-3), 5.20 (1H, t, J=4.6 Hz, H-6), 3.32 (1H, dd, J=4.8, 17.6 Hz, H-5), 3.06 (1H, dd, J=4.0, 18.0 Hz, H-5), 1.32 (3H, s, CH$_3$-7), 1.27 (3H, s, CH$_3$-7); $^{13}$C NMR (100 MHz, CDCl$_3$): δ$_C$ 166.9 (C-1'), 161.5 (C-2), 149.1 (C-8a), 148.7 (C-10a), 146.8 (C-7'), 146.1 (C-6'), 144.0 (C-3'), 139.6 (C-4), 126.9 (C-4'), 122.7 (C-5'), 122.2 (C-9'), 117.3 (C-4a), 116.4 (C-4b), 116.1 (C-10), 115.3 (C-8'), 114.4 (C-2'), 114.0 (C-3), 104.0 (C-9), 75.3 (C-7), 69.8 (C-6), 25.4 (C-5), 24.2 (CH$_3$-7), 22.8 (CH$_3$-7); IT-TOF/MS: m/z=409.1275 [M+H]$^+$, 431.1090 [M+Na]$^+$.

The candidates were examined for inhibitory activity against LMN A-progerin binding by an in vitro binding assay. As a result, JH4 and JH13 were found to block LMN A-progerin binding (FIG. 15C). The blocking ability of JH4 and JH13 was also demonstrated by GST-pull down assay using a cell lysate (FIG. 15D). However, JH4 did not disrupt the self association of LMN A, nor association between LMN A and LMN B (FIG. 15E). As a farensyl-transferase inhibitor (FTI-277) and rapamycin are known to ameliorate nuclear deformation, the effect of FTI on Prg-LMN A binding was examined. FTI was found to block the interaction, but slightly, as measured by GST-pull down assay (FIG. 2D). As for the specificity of the inhibitors, the JH compounds blocked interaction between Prg-p14/ARF (FIG. 16D), but did not disrupt the association of p53-p14/ARF (FIG. 16E). These results indicate that the JH compounds can specifically block Prg-LMN A binding or Prg-p14/ARF interaction, directly targeting progerin. Also, the compounds were analyzed for in vivo cellular effect by performing IP with a progerin antibody in HGPS fibroblasts after treatment with them for 24 hrs. As we expected, the JH compounds blocked interaction between progerin and LMN A/C (FIG. 15F), but did not alter the expression of progerin (FIG. 15G).

4) Effect and Molecular Mechanism of JH Compound

Figure 17:
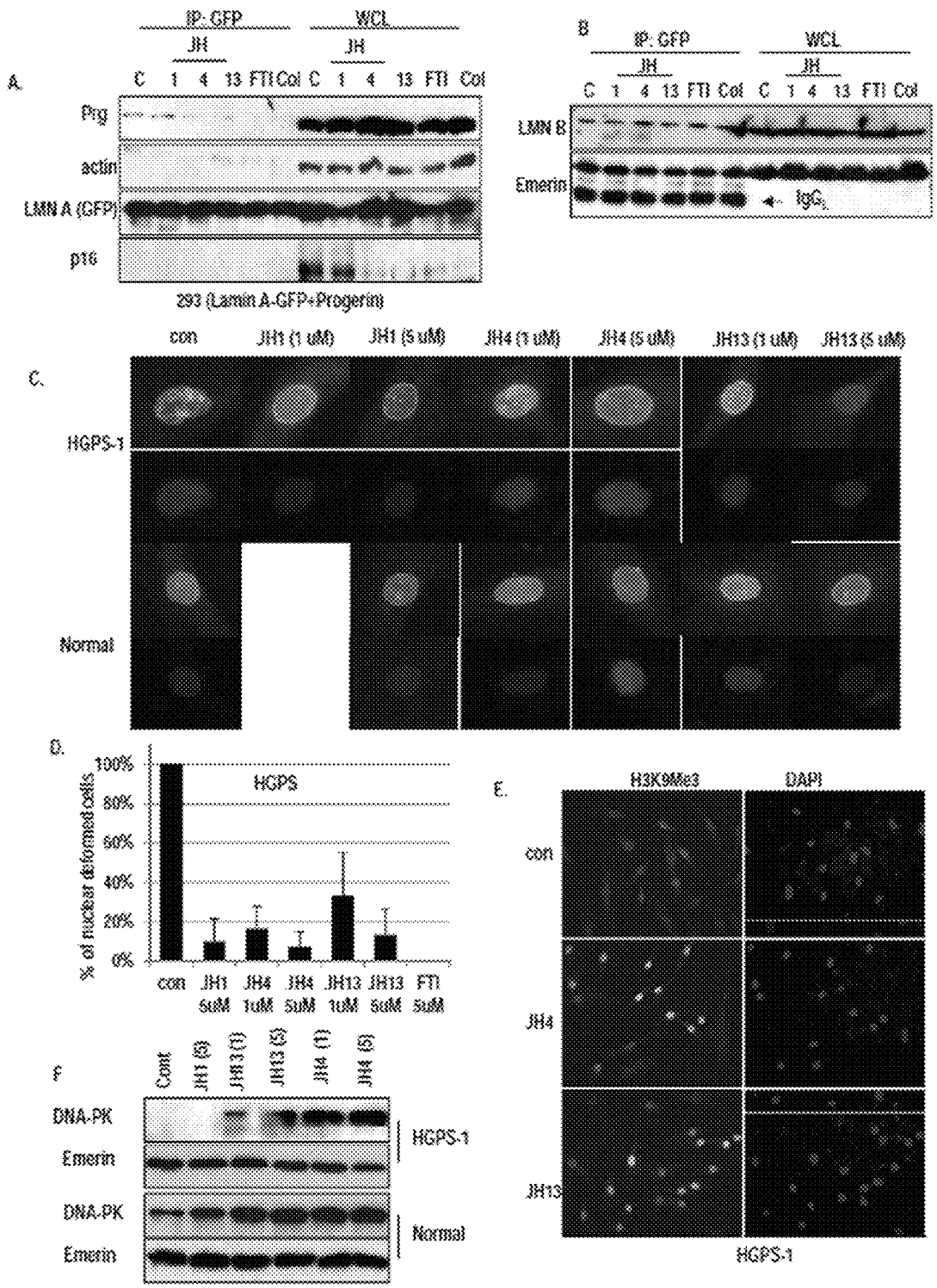
FIGS. 17 to 21 show the effects and molecular mechanism of the JH compounds of an embodiment of the present invention, as obtained in Example 2-10-4.
Figure 18:
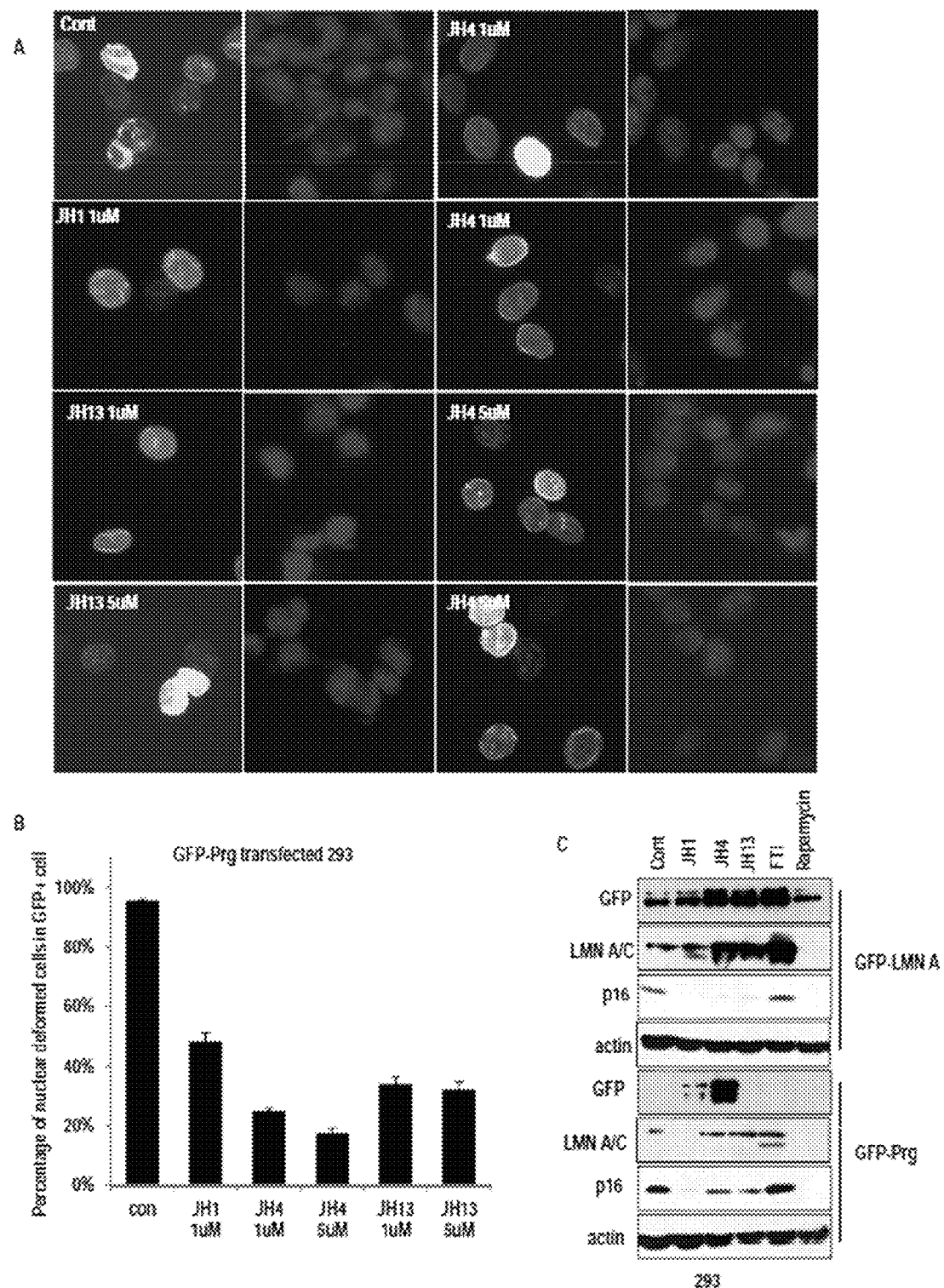
Figure 19:
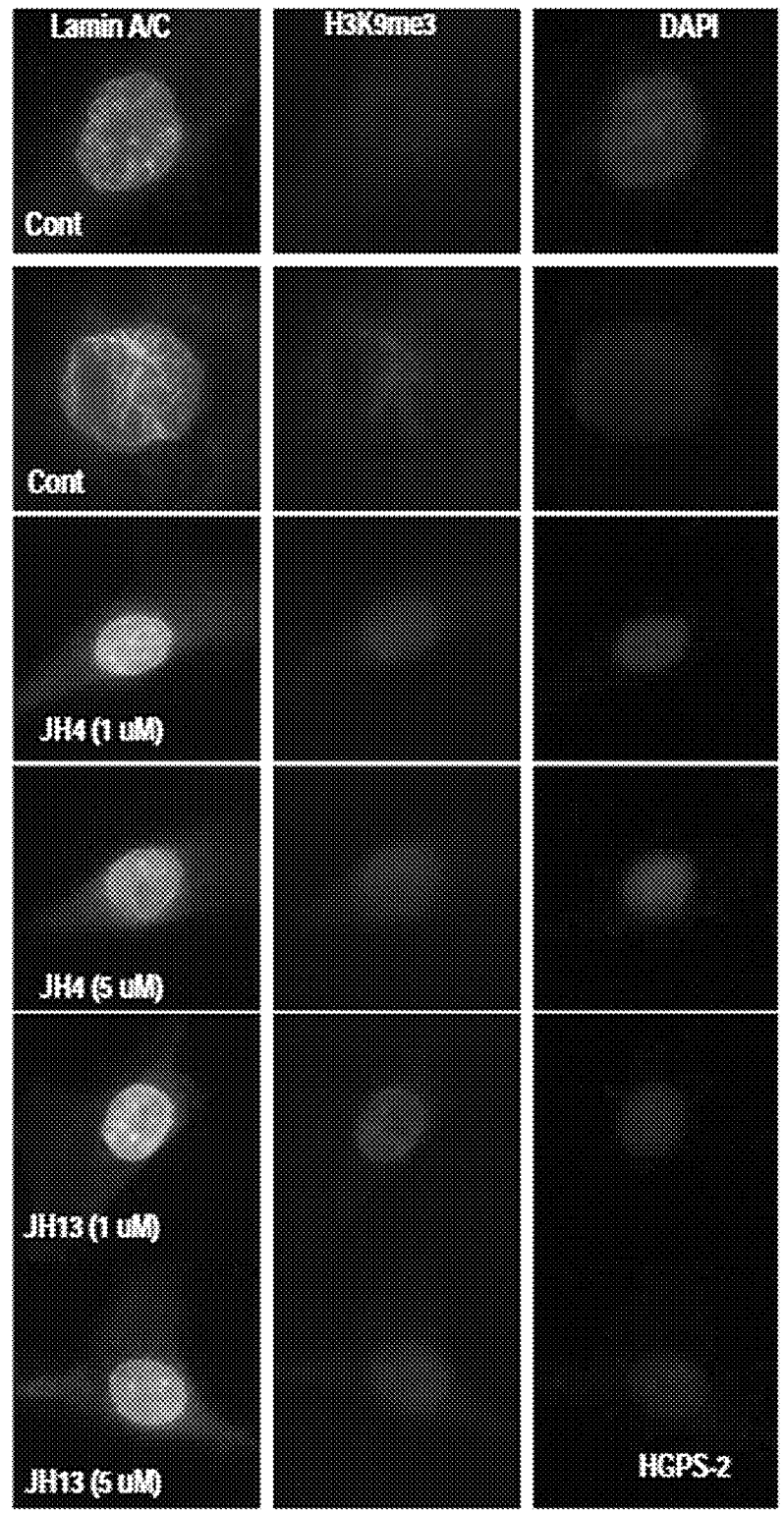
Figure 20:
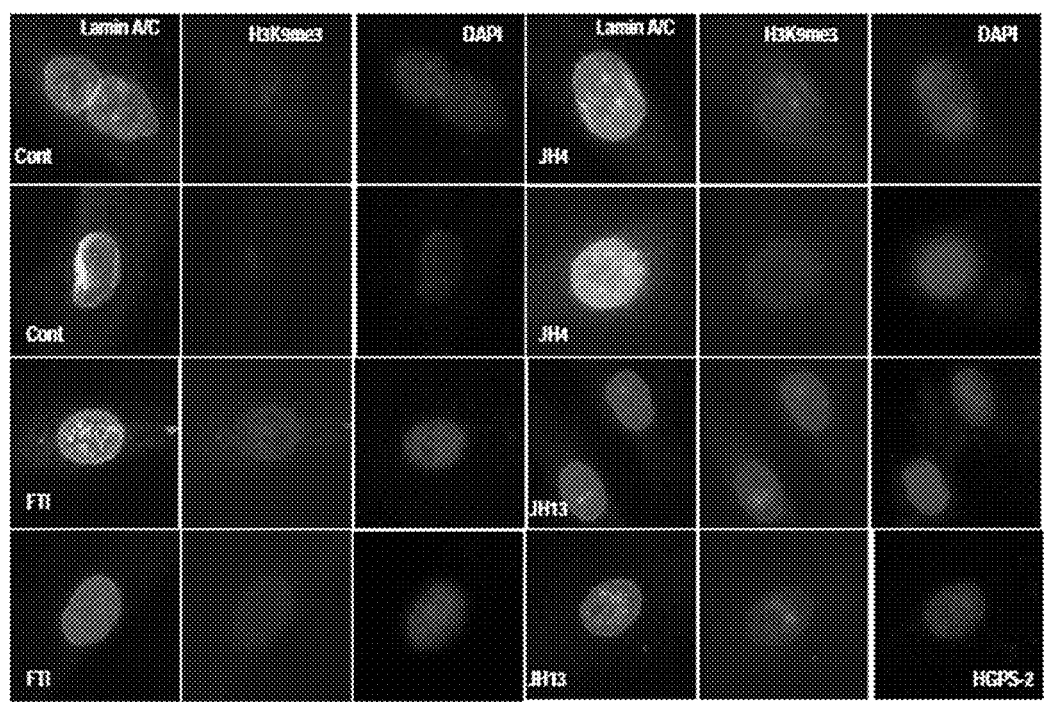
Figure 21:
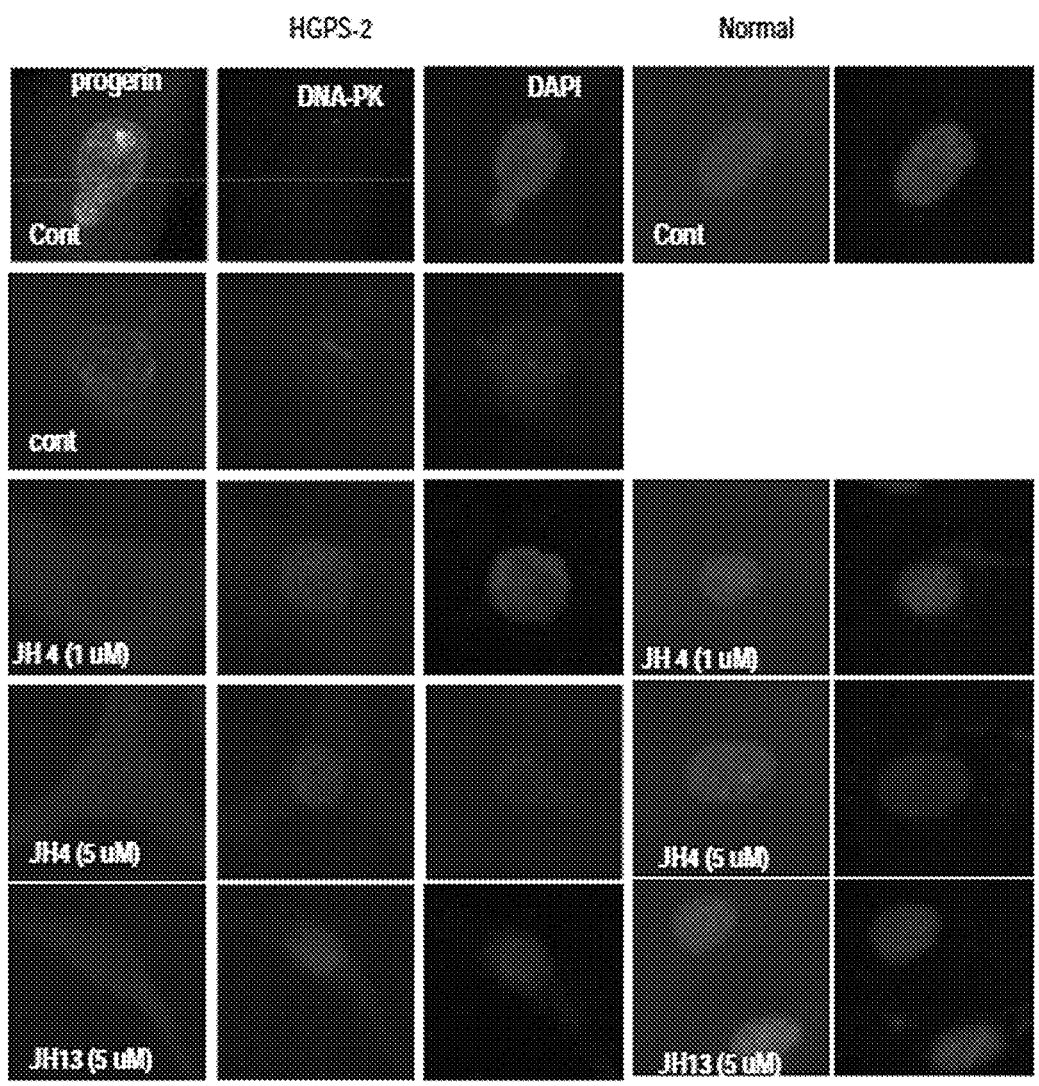

To further explore the molecular mechanism and effect of the JH compounds, IP was performed again with a GFP Ab in 293 cells after transfection with progerin and GFP-LMN A. LMN A-bound progerin was obviously reduced by the JH compounds (FIG. 17A). In contrast, binding between LMN A and LMN B, or Emerin was not affected by the compounds (FIG. 17B). In addition, a reduction in p16 expression was detected in response to the JH compounds (FIG. 17A). As LMN A/C dissociates during the G2/M phase, colcemide (Col) was used as a positive control. Also, the effect of FTI was compared with that of the JH compounds (FIGS. 17A and 17B). Indeed, the JH compounds were found to abolish the nuclear deformation (FIGS. 18A and 18B) while inducing the expression of LMN A/C (FIG. 18C). Moreover, they suppressed the p16 expression which is increased by Prg-transfection (FIG. 18C). To understand a more physiological significance, the nuclear LMN A/C was examined in two kinds of HGPS cells after incubation with the compounds for 24 hrs. JH1, JH4, and JH13 ameliorated the nuclear deformation (FIGS. 17C and 19). JH4 showed a more obvious effect than the other compounds (FIG. 17D), which is consistent with the previous data that JH4 could block the interaction of LMN A-Prg more effectively (FIG. 3D). To know whether an improvement in nuclear deformation could suppress cellular senescence, an examination was made of the trimethylation of lysine 9 on histone 3 (H3K9Me3), the reduction of which is regard as a marker of senescence. Interestingly, JH4 and JH13 increased the expression of H3K9Me3 in HGPS cells (FIGS. 17E and 19). As compared to FTI, JH4 and JH13 showed similar effects on the prevention of nuclear deformation and the induction of H3K9me3 (FIG. 20). Also, HGPS cells are characterized by a reduction in DNA-PK. As expected, DNA-PK expression was obviously increased in response to the JH compounds (FIGS. 17F and 21).

The data obtained above strongly suggest that the blockage of Prg-LMN A binding can ameliorate nuclear deformation and suppress cellular senescence.

5) Stimulative Effect of JH Compound on Cell Proliferation and Molecular Mechanism Thereof.

Figure 22:
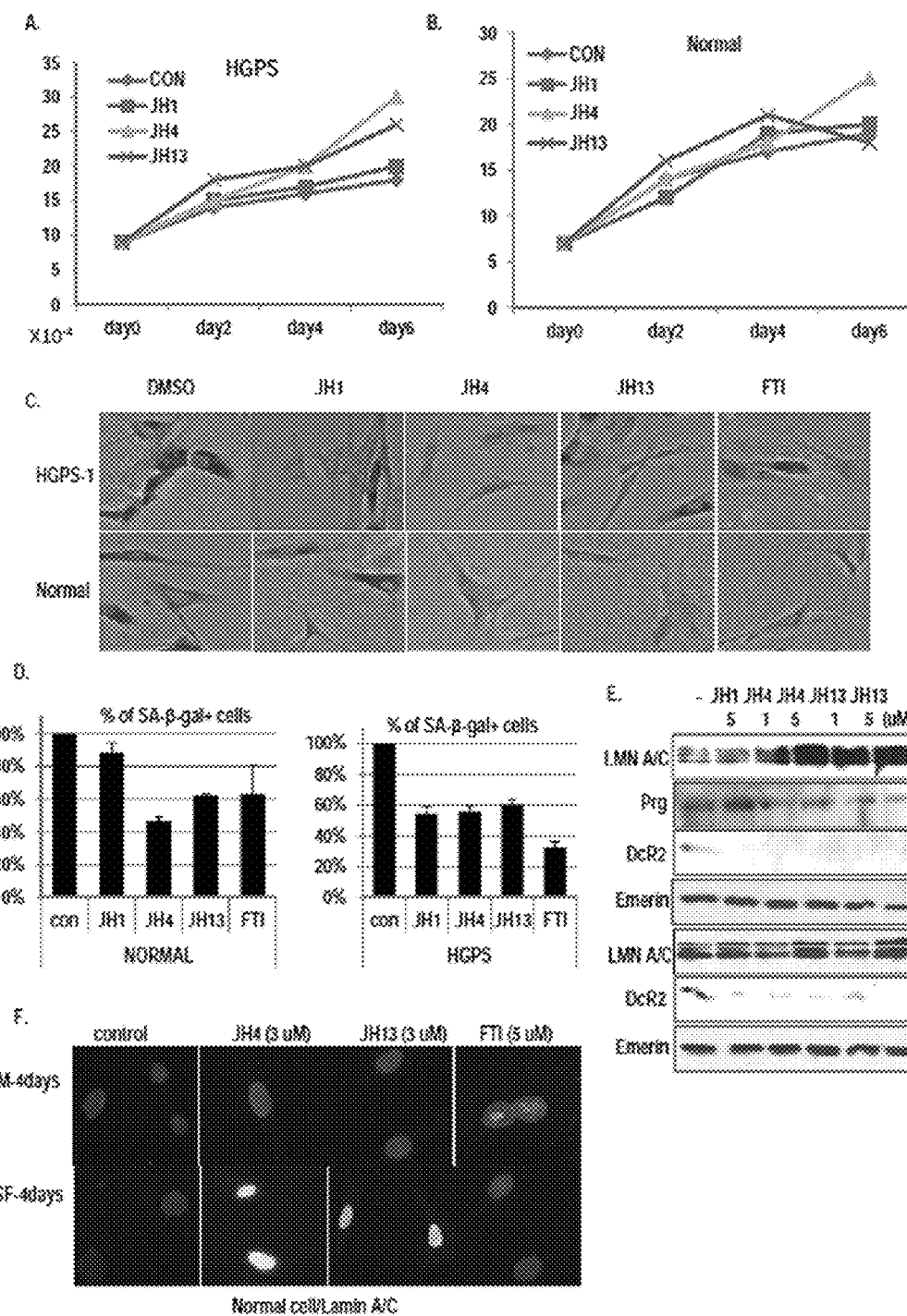
FIGS. 22 to 24 shows anti-senescence effects of the JH compounds according to one embodiment of the present invention in HGPS and normal cells, as obtained in Example 2-10-5.
Figure 23:
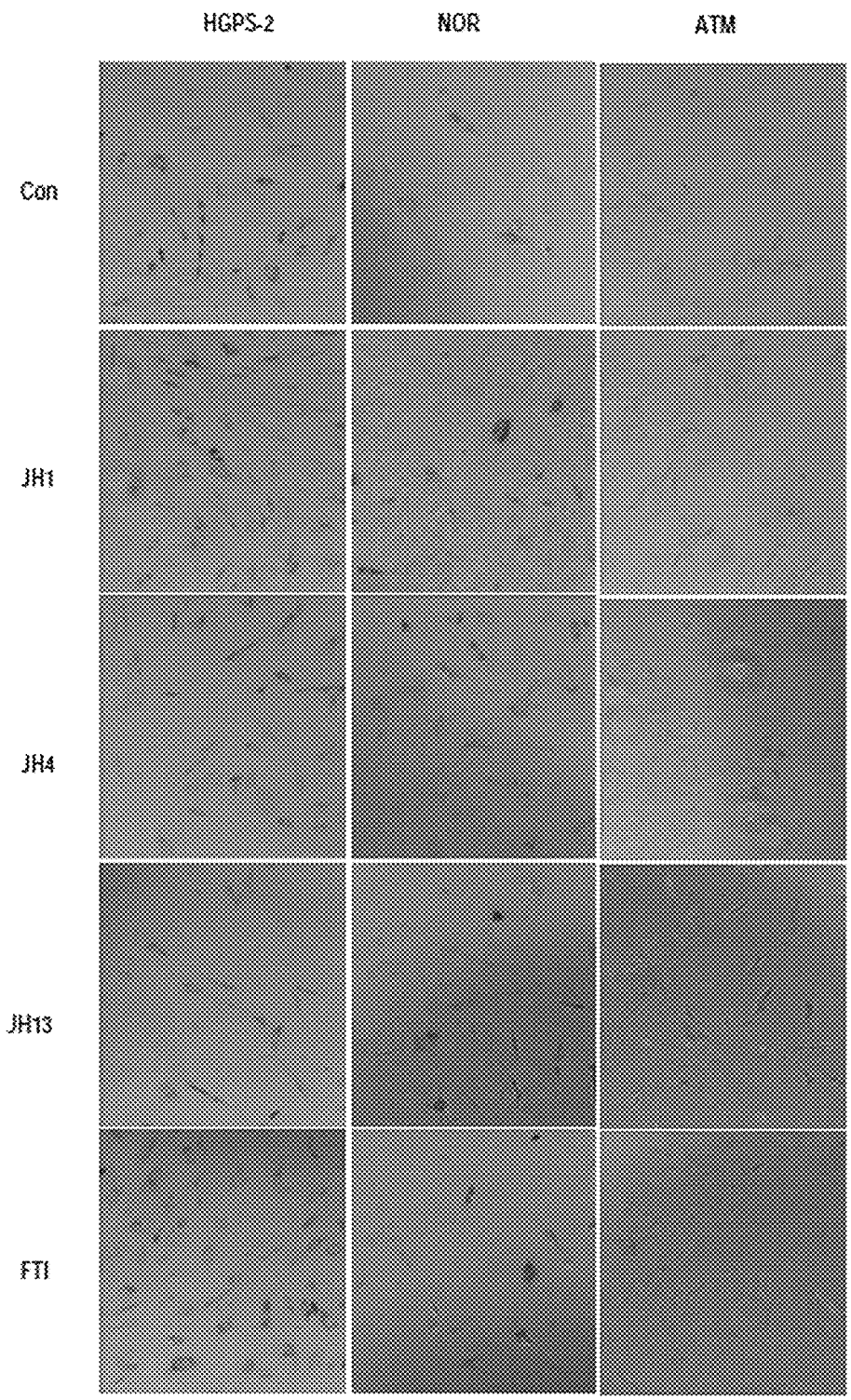
Figure 24:
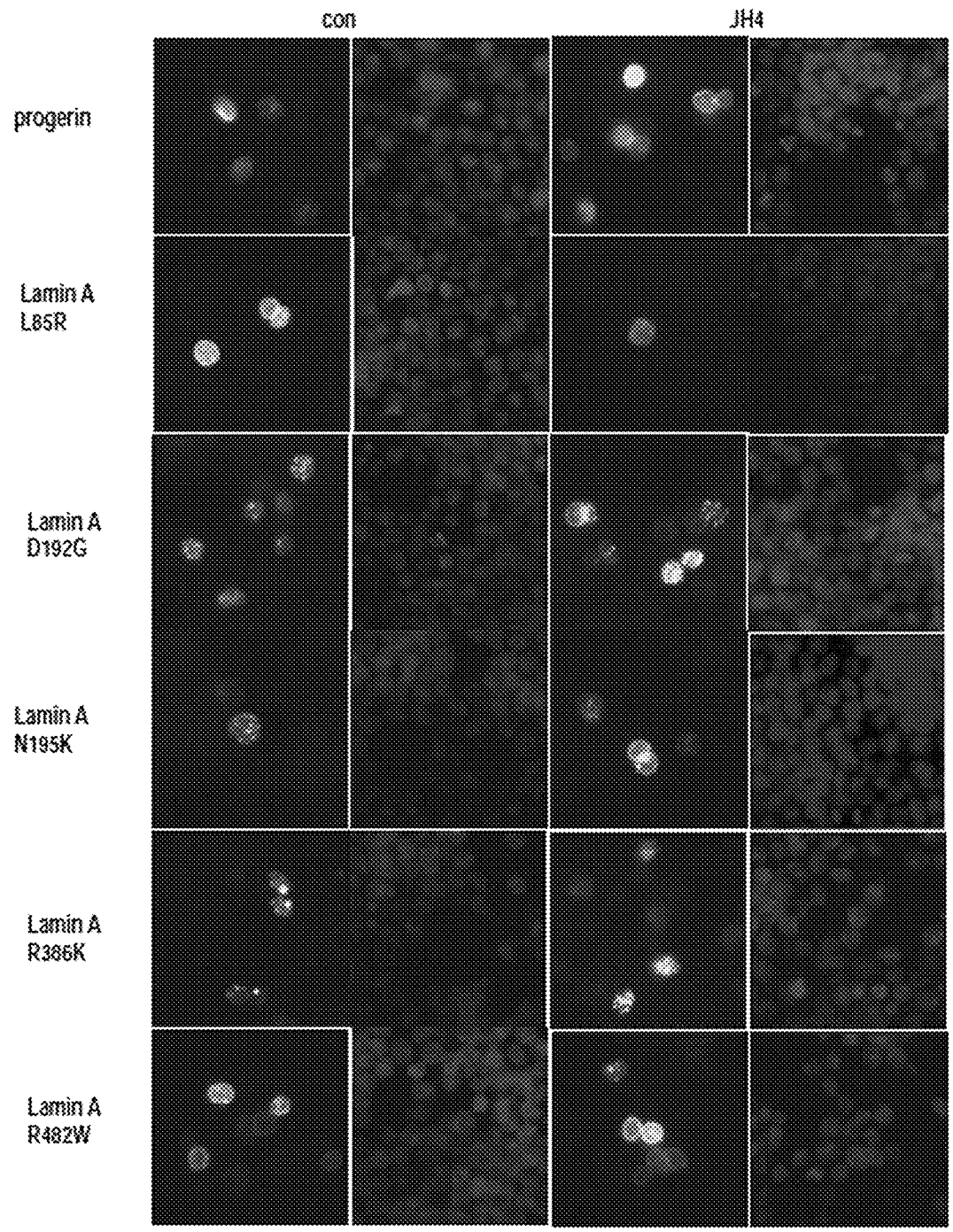

As cellular senescence is characterized by irreversible cell proliferation arrest, HGPS cells and normal fibroblasts were counted to check cell proliferation. As expected, the JH compounds (in particular JH4) promoted cell proliferation (FIG. 22A). More interestingly, JH4 induced cell proliferation in normal fibroblasts, as well (FIG. 22B). An experiment with senescence-specific β-galactosidase staining (SA-β-Gal) exhibited that the JH compounds (in particular JH4) could suppress SA-β-gal (FIGS. 22C and 23) in HGPS and normal cells. In HGPS cells, the JH compounds induced LMN A/C expression and reduced DcR2 expression (FIG. 22E). To address the effect of the JH compounds on normal cells, normal fibroblasts were incubated in a serum-free medium for 4 days. In the absence of the JH compounds, nuclear deformation was detected. In contrast, the JH compounds could induce the LMN A/C expression, and ameliorate nuclear deformation, but FTI could not (FIG. 22F). Several kinds of LMN A mutants are reportedly related with laminopathy. Effects of the JH chemicals on LMN A mutants were investigated. However, JH4 did not show a favorable effect on these mutants (FIG. 24).

Figure 25:
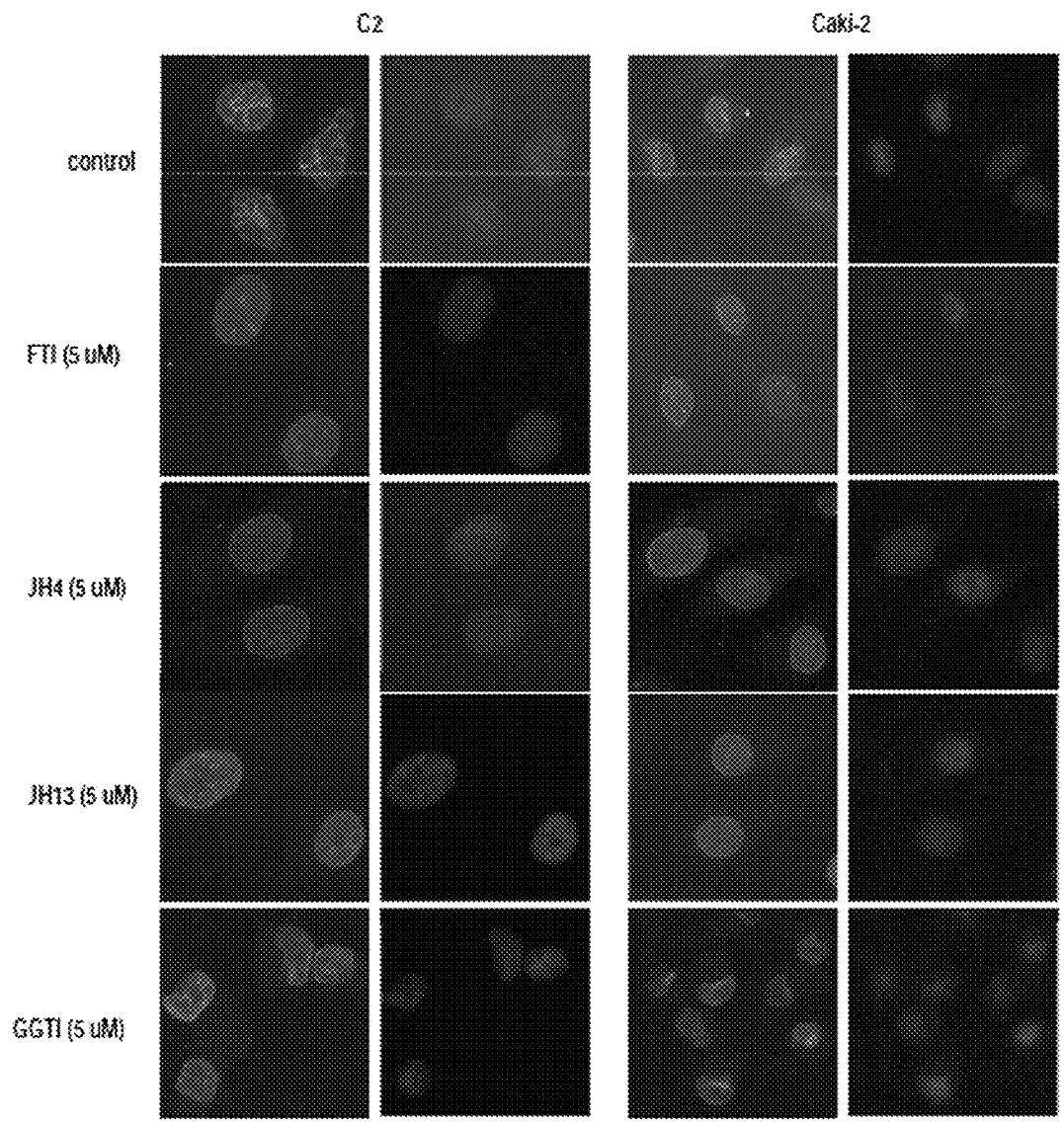
FIG. 25 shows the inhibitory effect of the JH compounds according to one embodiment of the present invention on nuclear irregularity, as obtained in Example 2-10-5.
Figure 26:
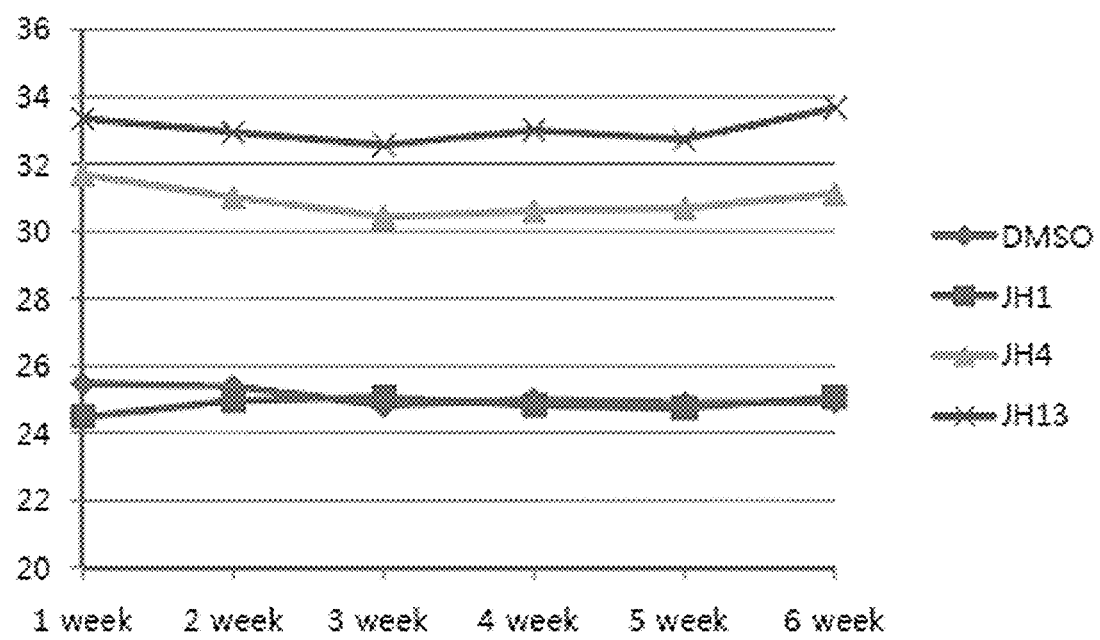
FIG. 26 is a graph showing in vivo toxicity of the JH compounds according to one embodiment of the present invention in mice.

Based on our observation that the nuclear irregularity of RCC is caused by progerin and improved by FTI, the JH compounds were also examined for effect on RCC. Like FTI, the JH compounds ameliorated nuclear irregularity (FIG. 25). These results suggested that the nuclear deformation of HGPS and the nuclear irregularity of RCC are evoked by progerin and that the Prg-induced senescence and nuclear deformation can be overcome by blocking Prg-LMN A binding. Also, the compounds of the present invention exhibited inhibitory activity against progerin-induced senescence as well as the senescence of normal cells. They were tested in vivo. Injection of JH chemicals for 6 weeks did not show obvious toxicity in the liver or kidney or cause a body weight loss (FIG. 26). This result suggests that the JH compounds induce neither obvious cytotoxicity (FIGS. 15B and 16C), nor in vivo toxicity.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby.

Sequence List Free Text

SEQ ID NO: 1 is a forward primer for Lamin A/C.
SEQ ID NO: 2 is a backward primer for Lamin A/C.
SEQ ID NO: 3 is a forward primer for GAPDH.
SEQ ID NO: 4 is a backward primer for GAPDH.

The invention claimed is:

1. A method for preventing or treating a progeria, comprising:

administering to a subject in need thereof a compound represented by the following Chemical Formula 1 or 2, or a pharmaceutically acceptable salt thereof as an active ingredient:

[Chemical Formula 1]

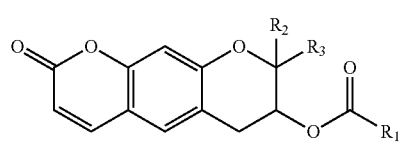

[Chemical Formula 2]

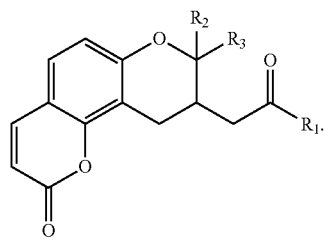

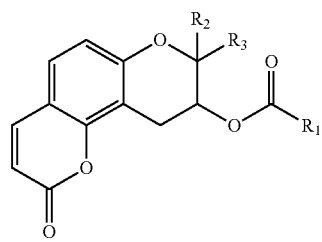

wherein,
$R_1$ is

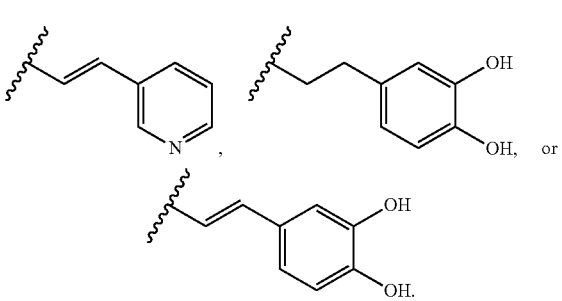

$R_2$ and $R_3$ are independently hydrogen or $C_{1-4}$ alkyl,
wherein the progeria is selected from the group consisting of a Werner syndrome and a Hutchinson-Gilford progeroid syndrome.

2. The method of claim 1, wherein the compound represented by Chemical Formula 1 or 2 inhibits binding between progerin and Lamin A.
3. The method of claim 1, wherein
R₁ is
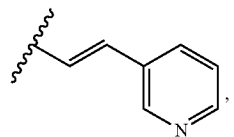 [SMILES: */C=C/c1cccnc1]
and
R₂ and R₃ are each methyl in Chemical Formula 1.
* * * * *